US009993570B2

(12) United States Patent
Mach et al.

(10) Patent No.: US 9,993,570 B2
(45) Date of Patent: Jun. 12, 2018

(54) RADIOLABELED TRACERS FOR POLY (ADP-RIBOSE) POLYMERASE-1 (PARP-1), METHODS AND USES THEREFOR

(71) Applicant: Washington University, Saint Louis, MO (US)

(72) Inventors: Robert Mach, Philadelphia, PA (US); Wenhua Chu, Saint Louis, MO (US); Dong Zhou, Ballwin, MO (US); Loren Michel, Clayton, MO (US); Delphine Chen, Brentwood, MO (US)

(73) Assignee: WASHINGTON UNIVERSITY, St. Louis, MO (US)

( * ) Notice: Subject to any disclaimer, the term of this patent is extended or adjusted under 35 U.S.C. 154(b) by 43 days.

(21) Appl. No.: 15/201,765

(22) Filed: Jul. 5, 2016

(65) Prior Publication Data
US 2016/0339124 A1 Nov. 24, 2016

Related U.S. Application Data

(63) Continuation of application No. PCT/US2015/010129, filed on Jan. 5, 2015.

(60) Provisional application No. 61/923,759, filed on Jan. 5, 2014.

(51) Int. Cl.
*A61K 51/00* (2006.01)
*A61K 51/04* (2006.01)
*C07D 403/12* (2006.01)
*C07D 235/18* (2006.01)
*C07D 487/04* (2006.01)
*A61B 6/03* (2006.01)

(52) U.S. Cl.
CPC .......... *A61K 51/0468* (2013.01); *A61B 6/037* (2013.01); *C07D 235/18* (2013.01); *C07D 403/12* (2013.01); *C07D 487/04* (2013.01)

(58) Field of Classification Search
CPC .. A61K 51/0468; A61B 6/037; C07D 403/12; C07D 235/18; C07D 487/04
USPC ....................................................... 424/1.89
See application file for complete search history.

(56) References Cited

U.S. PATENT DOCUMENTS

| 6,548,494 B1 * | 4/2003 | Webber ................ C07D 487/06 514/220 |
| 7,781,596 B1 | 8/2010 | Lubisch et al. |
| 7,956,064 B2 | 6/2011 | Chua et al. |
| 2009/0068105 A1 | 3/2009 | Mach et al. |
| 2012/0171119 A1 | 7/2012 | Mach et al. |
| 2015/0216168 A1 | 8/2015 | Frackenpohl et al. |

FOREIGN PATENT DOCUMENTS

| WO | 2000042040 A1 | 7/2000 | |
| WO | 200116136 A2 | 3/2001 | |
| WO | 2004/096793 A1 | 11/2004 | |
| WO | WO 2006067376 A2 * | 6/2006 | ........... A61K 51/088 |
| WO | 2014037340 A1 | 3/2013 | |

OTHER PUBLICATIONS

Reiner et al. Angew. Chem. Int. Ed. 2011, 50, 1922-1925.*
Lasne et al. Top. Curr. Chem. 2002, 201-258.*
Zhang et al. Curr. Top. Med. Chem. 2007, 7, 1817-1828.*
White et al. J. Med. Chem. 2000, 43, 4084-4097.*
Basu, B., et al., PARP inhibitors: mechanism of action and their potential role in the prevention and treatment of cancer., Drugs, 2012, 72, 1579-1590.
DeLaney, C. A., et al., Potentiation of temozolomide and topotecan growth inhibition and cytotoxicity by novel poly (adenosine diphosphoribose) polymerase inhibitors in a panel of human tumor cell lines., Clinical Cancer Research, 2000, 6, 2860-2867.
Ferraris, D. V., Evolution of poly(ADP-ribose) polymerase-1 (PARP-1) inhibitors. From concept to clinic., Journal of Medicinal Chemistry, 2010, 53, 4561-4584.
Gelmon, K. A., et al., Olaparib in patients with recurrent high-grade serous or poorly differentiated ovarian carcinoma or triple-negative breast cancer: a phase 2, multicentre, open-label, non-randomised study., The Lancet Oncology 2011, 12, 852-861.
Glaser, M.; Arstad, E. "Click labeling" with 2-[18F]fluoroethylazide for positron emission tomography., Bioconjugate Chemistry 2007, 18, 989-993.
Jagtap, P. et al., Novel phenanthridinone inhibitors of poly (adenosine 5'-diphosphate-ribose) synthetase: potent cytoprotective and antishock agents., Critical Care Medicine, 2002, 30, 1071-1082.
Keliher, E. J., et al., High-yielding, two-step 18F labeling strategy for 18F-PARP1 inhibitors., ChemMedChem., 2011, 6, 424-427.
Kinoshita, T., et al., Inhibitor-induced structural change of the active site of human poly(ADP-ribose) polymerase., FEBS Letters, 2004, 556, 43-46.
Kummar, S, et al., Phase I study of PARP inhibitor ABT-888 in combination with topotecan in adults with refractory solid tumors and lymphomas., Cancer Research 2011, 71, 5626-5634.
Lasne M.C. et al., Chemistry of β+-emitting compounds based on fluorine-18. Top. Curr. Chem., 2002, 222, 201-258.
Liu, X et al., Iniparib nonselectively modifies cysteine-containing proteins in tumor cells and is not a bona fide PARP inhibitor., Clinical Cancer Research, 2012, 18, 510-523.

(Continued)

*Primary Examiner* — Michael G Hartley
*Assistant Examiner* — Sean R Donohue
(74) *Attorney, Agent, or Firm* — Thompson Coburn LLP; Charles P. Romano

(57) ABSTRACT

Disclosed are PARP-1 inhibitors, which can be $^{18}$F-labeled for use as tracers in positron emission tomographic (PET) imaging. Further disclosed are methods of synthesis. Of the compounds synthesized, 2-[p-(2-Fluoroethoxy)phenyl]-1.3.10-triazatricyclo[6.4.1.0$^{4,13}$]trideca-2,4(13),5,7-tetraen-9-one (12) had the highest inhibition potency for PARP-1 (IC$_{50}$=6.3 nM). Synthesis of [$^{18}$F]-12 is disclosed under conventional conditions in high specific activity with 40-50% decay-corrected yield. MicroPET imaging using [$^{18}$F]-12 in MDA-MB-436 tumor-bearing mice demonstrated accumulation of [$^{18}$F]-12 in a tumor. Binding, can be blocked by olaparib. The compounds have utility for tumor imaging.

5 Claims, 12 Drawing Sheets

(56) References Cited

OTHER PUBLICATIONS

Menear, K. A., et al., 4-[3-(4-cyclopropanecarbonylpiperazine-1-carbonyl)-4-fluorobenzyl]-2H-phthalazin-1-one: a novel bioavailable inhibitor of poly(ADP-ribose) polymerase-1. Journal of Medicinal Chemistry 2008, 51, 6581-6591.

Plummer, R., et al., A phase II study of the potent PARP inhibitor, Rucaparib (PF-01367338, AG014699), with temozolomide in patients with metastatic melanoma demonstrating evidence of chemopotentiation., Cancer Chemotherapy and Pharmacology, 2013, 71, 1191-1199.

Reiner, T. et al., Synthesis and in vivo imaging of a 18F-labeled PARP1 inhibitor using a chemically orthogonal scavenger-assisted high-performance method., Angew Chem. Int. Ed. Engl., 2011, 50, 1922-1925.

Reiner, T., et al., Imaging therapeutic PARP inhibition in vivo through bioorthogonally developed companion imaging agents., Neoplasia, 2012, 14, 169-177.

Ruf, A. et al., Inhibitor and NAD+ binding to poly(ADP-ribose) polymerase as derived from crystal structures and homology modeling., G. E. Biochemistry 1998, 37, 3893-3900.

Sandhu, S. K.et al., The poly(ADP-ribose) polymerase inhibitor niraparib (MK4827) in BRCA mutation carriers and patients with sporadic cancer: a phase 1 dose-escalation trial., The Lancet Oncology 2013, 14, 882-892.

Skalitzky, D. J. et al., Tricyclic benzimidazoles as potent poly(ADP-ribose) polymerase-1 inhibitors, Journal of Medicinal Chemistry 2003, 46, 210-213.

Tu, Z., et al., Synthesis and in vivo evaluation of [11C]PJ34, a potential radiotracer for imaging the role of PARP-1 in necrosis., Nuclear Medicine and Biology 2005, 32, 437-443.

Tu, Z., et al., Synthesis and in vitro and in vivo evaluation of 18F-labeled positron emission tomography (PET) ligands for imaging the vesicular acetylcholine transporter., J. Med. Chem. 2009, 52, 1358-1369.

Takesh, M., et al., Diagnostic Role of 18F-FECH-PET /CT Compared with Bone Scan in Evaluating the Prostate Cancer Patients Referring with Biochemical Recurrence, ISRN Oncology, vol. 2012 (2012), Article ID 815234.

Wahlberg, E.et al., Family-wide chemical profiling and structural analysis of PARP and tankyrase inhibitors., J. Nature Biotechnology, 2012, 30, 283-288.

White, A. W., et al., Resistance-modifying agents. 9. Synthesis and biological properties of benzimidazole inhibitors of the DNA repair enzyme poly(ADP-ribose) polymerase., Journal of Medicinal Chemistry, 2000, 43, 4084-4097.

\* cited by examiner

PJ-34 (1) ($IC_{50}$ = 20 nM)

NU1085 (2) ($K_i$ = 6 nM)

AG014361 (3) ($K_i$ = 5.8 nM)

AZD2281, olaparib (4) ($IC_{50}$ = 5 nM)

Red Channel

Blue Channel

Composite

Time ( min)

RADIOLABELED TRACERS FOR POLY (ADP-RIBOSE) POLYMERASE-1 (PARP-1), METHODS AND USES THEREFOR

CROSS-REFERENCE TO RELATED APPLICATIONS

This application is a continuation of PCT/US15/10129, filed Jan. 5, 2015. PCT/US15/10129 claims benefit of and priority to U.S. Provisional Application Ser. No. 61/923,759 filed on Jan. 5, 2014, each of which is incorporated by reference in its entirety.

STATEMENT REGARDING FEDERALLY SPONSORED RESEARCH OR DEVELOPMENT

This invention was made with government support under HL013851 and HL116389 awarded by the National Institutes of Health. The government has certain rights in the invention.

TECHNICAL FIELD

The present teachings are in the field of radiolabeled tracers for imaging PARP-1 distribution.

INTRODUCTION

Poly (ADP-ribose) polymerase-1 (PARP-1) is one of the most abundant members of the PARP family of nuclear enzymes.[1] Its best characterized functions are sensing DNA damage and facilitating DNA repair, but PARP-1 also participates in many other DNA-related cellular processes, such as apoptosis regulation, cell division, differentiation, transcriptional regulation, and chromosome stabilization.[2-5] PARP-1 may also play a central role in regulating inflammatory responses. PARP-1, a 113 kD protein, has three unique structural domains: the N-terminal DNA binding domain with two zinc fingers that specifically bind to damaged DNA strand breaks;[1,6] the central automodification domain; and the C-terminal catalytic domain that sequentially transfers ADP-ribose subunits from nicotinamide adenine dinucleotide (NAD$^+$) to protein acceptors. Due to its critical role in DNA repair, PARP-1 has been actively pursued as a drug target over the past 20 years, with tremendous efforts invested to develop several generations of PARP-1 inhibitors (FIG. 1) for therapeutic purposes, especially in the area of ischemia-reperfusion injury and cancer.[5,8] More recently, PARP1 inhibition has been demonstrated as an effective method for inducing synthetic lethality in cancers that depend on PARP1 activity for survival.[9] Additionally, PARP inhibitors or the absence of PARP expression in transgenic mice reduces the degree of inflammation present and thus protects various organs, including the lungs, from the detrimental effects of persistent inflammation. Therefore, a number of PARP inhibitors, including olaparib (AZD2281

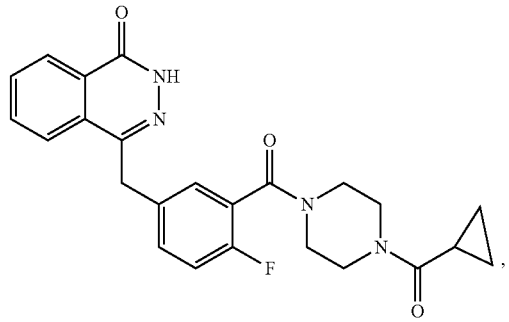 [SMILES: O=C(c1cc(Cc2n[nH]c(=O)c3ccccc23)ccc1F)N1CCN(C(=O)C2CC2)CC1]

KU-59436), veliparib (ABT-888), rucaparib (PF-01367338, AG014699), and niraparib (MK4827), are now undergoing evaluation in clinical trials as anticancer drugs[10-14]. These PARP inhibitors effectively inhibit PARP1 activity as well as activity of other PARP-like enzymes such as PARP2 and tankyrase1[15]. Other PARP inhibitors include benzimidazole carbox amide (NU1085)[21] and its derivative (AG014361).[22]

Despite the promising results from clinical trials related to progression-free survival however, differences in the ability of the various PARP inhibitors to suppress tumoral PARP activity cars not be accurately determined by current assays. Additionally, the mechanism of action for iniparib

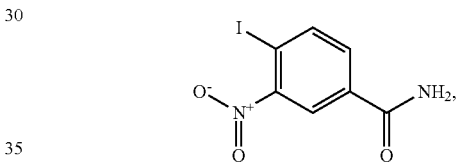

initially developed as a PARP inhibitor, was more recently discovered to be most likely unrelated to inhibition of PARP activity[16]. Therefore, methods for quantifying tumoral PARP activity noninvasively in vivo are needed for demonstrating tumor-specific PARP inhibition as well as assessing the duration of effective PARP inhibition to guide dosing decisions.

Imaging with positron emission tomography (PET) could be an effective approach for noninvasively determining PARP activity levels. [$^{11}$C]PJ-34, a PARP-1 targeted tracer, showed some potential in imaging PARP-1 expression in an animal model of diabetes.[17] Recently, a $^{18}$F-labeled olaparib/AZD2281 derivative was synthesized by a two-step labeling strategy using a [4+2] cycloaddition between trans-cyclooctene and tetrazine and was used in in vitro cell studies and microPET tumor imaging.[18-20]

SUMMARY

In various embodiments, the present teachings include radiolabeled PARP-1 inhibitors for measuring PARP-1 expression and imaging PARP-1 distribution in vivo with PET. In various embodiments, the present teachings include various compounds that bind PARP-1 and are labeled with a positron-emitting radionuclide such as $^{18}$F. In various embodiments, methods of synthesis of the compounds are also disclosed. Also disclosed are the inhibition potencies against PARP-1 of compounds of the present teachings.

In some configurations, 2-[p-(2-Fluoroethoxy)phenyl]-1.3.10-triatricyclo[6.4.1.0⁴,¹³]trideca-2,4(13),5,7-tetraen-9-one

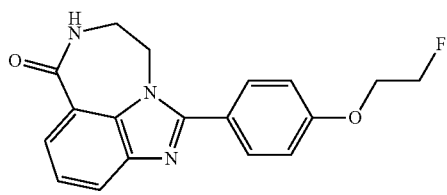
(12)

(IC$_{50}$=6.3≠1.3 nM) can be labeled with ¹⁸F. In various configurations, the ¹⁸F labeling can be in one step and can provide high chemical and radiochemical purities. In some configurations, microPET imaging can be used to demonstrate increased uptake of [¹⁸F]12 in MDA-MB-436 tumors in some configurations, this increased uptake can be blocked by both 12 and olaparib/AZD2281.

In various embodiments, a PARP-1 inhibitor 12 (IC$_{50}$=6.3 nM) has been developed. [¹⁸F]12 can be synthesized using conventional labeling methods with high purities and specific activity. MicroPFT studies of [¹⁸F]12 in MBA-MD-436 tumor-bearing mice demonstrated accumulation of the radioactivity in these tumors which are known to overexpress PARP-1. Tumor uptake can be blocked by PARP-1 inhibitor olaparib and by 12, supporting the specificity of [¹⁸F]12 uptake for PARP-1, activity. [¹⁸F]12 can thus be useful as a PET tracer for imaging PARP-1 expression in vivo.

In various embodiments, incorporation of the radionuclide can be achieved either through a fluoroethoxy group via nucleophilic substitution²⁸ with [¹⁸F]fluoride, or via Cu(I) catalyzed click reaction using 2-[¹⁸F]fluoroethyl azide.²⁹,³⁰ The corresponding 2-fluoroethoxy and 2-fluoroethyl triazole analogs of NU1085 and AG014361 can be synthesized according to Schemes 1 and 2, respectively, in only a few steps. Although, the propargyl and triazole groups slightly reduced the inhibition potency of the analogs, the most potent of these were 12 (IC$_{50}$=63 nM), with a 2-fluoroethoxy group, followed by

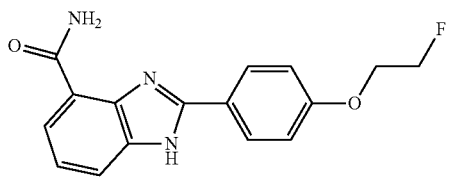
(8)

(IC$_{50}$=10.8).

In some configuration, the one-stop labeling of [¹⁸F]12 under typical conditions can be automated for clinical production of this tracer. In some configurations, the final dose for injection can have high chemical and radiochemical purities and can have excellent specific activity. In various configurations, the injected mass of [¹⁸F]12 in the microPET studies can be 0.0037-0.012 μg/dose (0.2 mCi/dose), winch can be much lower than the blocking dose and therapeutic doses. This amount of mass can be unlikely to have a pharmacological effect. [¹⁸F]12 can thus be useful as a PET tracer for imaging PARP-1 expression and tumors. In some configurations, a PARP-1 tracer such as [¹⁸F]12 can also be useful to identify patients with chronic inflammatory diseases in whom PARP inhibitor treatments could potentially retard the progression of the inflammatory disease.

The present teachings thus include compounds and pharmaceutically acceptable salts thereof, of structure

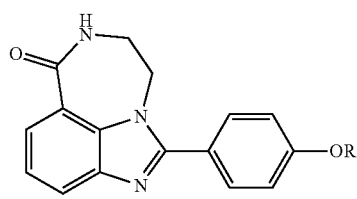

or of structure

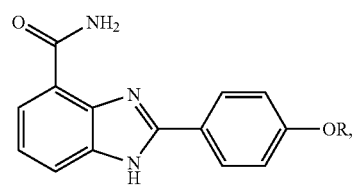

wherein R can be selected from the group consisting of

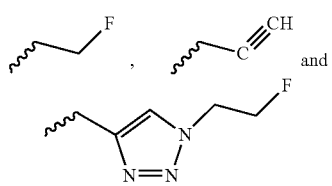

wherein

represents a bond. In some configurations, R can be

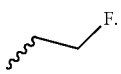

In some configurations, the F can be an ¹⁸F. In some configurations. R can be

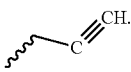

In some configurations, R can be

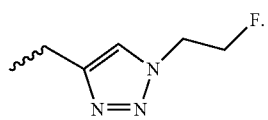

In some embodiments, the present teachings include methods of imaging a tumor in a subject, as well as methods of imaging inflammation in a subject. In various configurations, these methods can comprise administering to a subject a compound of structure or of structure wherein R can be selected from the group consisting of wherein represents a bond. In some configurations, R can be In some configurations, the F can be an $^{18}$F. In some configurations, R can be In some configurations, R can be wherein the compound comprises a positron-emitting radionuclide such as $^{18}$F. The methods can further include subjecting the subject PET scanning.

In various configurations of the present teachings, a subject can be a human having, or suspected of having, a tumor or inflammation. A subject can also be an animal having, or suspected of having, a tumor or inflammation. The animal can be a mammal, for example a companion animal such as, for example, a cat or dog, a laboratory animal such as, for example, a mouse, guinea pig, rabbit or rat, or a large animal such as, for example, horse, a sheep, a cow, or a goat.

DETAILED DESCRIPTION

Figure 1:
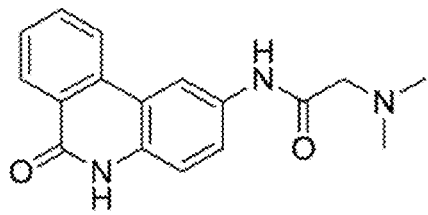
FIG. 1 illustrates examples of PARP-1 inhibitors (prior art).
Figure 1:
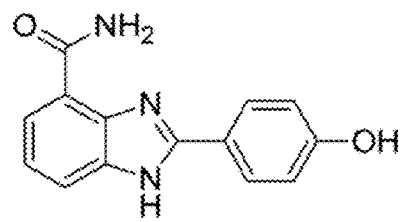
Figure 1:
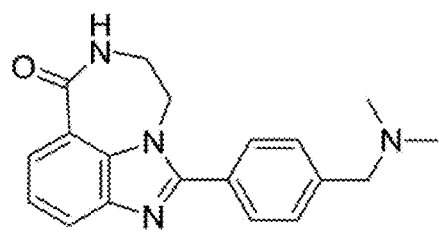
Figure 1:
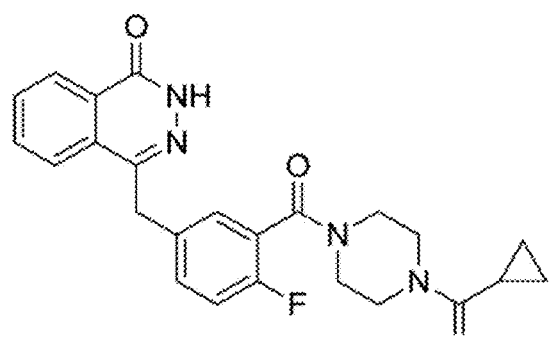

The present teachings in various embodiments include tracers that can be used for imaging of tumors or of inflammation by PFT scanning. In various aspects, the tracers can bind PARP-1 with high affinity. In various embodiments, the present teachings also include methods of synthesis of the tracers. Tracers of the present teachings, when labeled with a positron-emitting radioisotope such as $^{18}$F, can be administered to a subject by intravenous or other suitable means.

The methods described herein utilize laboratory techniques well known to skilled artisans, and guidance can be found in laboratory manuals and textbooks such as Sambrook, J., et al., Molecular Cloning: A Laboratory Manual 3rd ed. Cold Spring Harbor Laboratory Press, Cold Spring Harbor, N.Y., 2001; Spector, D. L. et al., Cells: A Laboratory Manual, Cold Spring Harbor Laboratory Press, Cold Spring Harbor, N.Y. 1998; Hendrickson et al., Organic Chemistry 3rd edition, McGraw Hill, New York, 1970; Carruthers, W., and Coldham, I., Modern Methods of Organic Synthesis (4th Edition), Cambridge University Press, Cambridge, U.K., 2004; Curati, W. L., Imaging in Oncology, Cambridge University Press, Cambridge, U.K., 2004; Welch, M. J., and Redvanly, C. S., eds. Handbook of Radiopharmaceuticals: Radiochemistry and Applications, J. Wiley, New York, 2003. Methods of administration of pharmaceuticals and dosage regimes, can be determined according to standard principles of pharmacology well known skilled artisans, using methods provided by standard reference texts such as Remington: the Science and Practice of Pharmacy (Alfonso R, Gennaro ed. 19th ed. 1995): Hardman, J. G., et al., Goodman & Gilman's The Pharmacological Basis of Therapeutics, Ninth Edition, McGraw-Hill, 1996; and Rowe, R. C., et al. Handbook of Pharmaceutical Excipients, Fourth Edition, Pharmaceutical Press, 2003.

In the experiments described herein, reagents and materials were purchased from commercial suppliers and used without further purification unless otherwise stated. Chemicals were purchased from Sigma-Aldrich Chemical Co. (St. Louis, Mo. USA) unless otherwise specified. All reactions were earned out by standard air-free and moisture-free techniques under an inert nitrogen atmosphere with dry solvents unless otherwise stated.

Flash column chromatography can be conducted using a variety of methods and instruments including Scientific Adsorbents, Inc. silica gel, 60A. "40 Micron Flash" (32-63 μm). Melting points can be determined using a variety of methods and instruments well known in the art, including the MEL-TEMP 3.0 apparatus. In some configurations, melting point data is uncorrected. $^1$H and $^{13}$C NMR spectra at 300 MHz can be recorded through a variety of routine methods on a variety of instruments, including a Varian Mercury-VX spectrometer. In some configurations, chemical shifts can be reported as parts per million (ppm) downfield from tetramethylsilane (TMS). All coupling constants (J) are given in Hertz (Hz). Splitting patterns are typically described as follows: s, singlet; d, doublet: t, triplet; m, multiplet.

Elemental analysis (C, H, N) can be determined by a variety of commercial contract organizations such as Atlantic Microlab, Inc., Norcross, Ga. High performance liquid chromatography (HPLC) can be performed with an ultraviolet detector and a well-scintillation NaI (TI) detector and associated electronics for radioactivity detection. A Grace Altima C18 250×10 mm 10μ semi-preparative column (A) and au Altima C18 250×4.6 mm 10μ analytical column (B) can be used for preparation and analysis respectively. [$^{18}$F] Fluoride can be produced by the $^{18}$O(p,n)$^{18}$F reaction through proton irradiation of enriched (95%) [$^{18}$O] water in the RDS111 cyclotron. Radio-TLC can be accomplished using a Bioscan AR-2000 imaging scanner (Bioscan, Inc., Washington, D.C.). Published methods were used for the synthesis of compound 5[27] and 11[22]. All animal experiments were conducted under Washington University Animal Studies Committee IACUC-approved protocols in accordance with the recommendations of the National Research Council's 'Guide for the Care and Use of Laboratory Animals'.

EXAMPLES

The present teachings including descriptions provided in the Examples that are not intended to limit the scope of any claim. Unless specifically presented in the past tense, an example can be a prophetic or an actual example. The following non-limiting examples are provided to further illustrate the present teachings. Those of skill in the art, in light of the present disclosure, will appreciate that many changes can be made in the specific embodiments that are disclosed and still obtain a like or similar result without departing from the spirit and scope of the present teachings.

Example 1

This example illustrates synthesis of PARP-1 inhibitors. Compound numbers refer to Schemes 1 and 2, infra.

The syntheses of PARP-1 inhibitors of the present teachings are shown in Schemes 1 and 2. Methyl 2,3-diaminobenzate (5) was reacted with 4-(2-fluoroethoxy)benzoyl chloride in pyridine and dichloromethane to afford a mixture of intermediate 6a and the benzimidazole compound 6. After evaporation of the solvent, the mixture was refluxed with methanesulfonic acid in methanol to give 6. Then the methyl ester of 6 was compound to the amide compound 8 using ammonium in methanol. Similarly, the alkyne analog 9 was synthesized starting from 5 and 4-(prop-2-ynyloxy)benzoyl chloride. The triazole compound 10 was prepared by the copper(I) catalyzed click reaction of 2-fluoroethylazide and 9 using CuSO$_4$.5H$_2$O and sodium ascorbate in DMF.

The tricycle compounds were synthesized from the diamine intermediate 11. Compound 11 was reacted with 4-(2-fluoroethoxy)benzoyl chloride in pyridine and dichloromethane to afford a mixture of intermediate 12a and the benzimidazole 12. After evaporation of the solvent, the mixture was refluxed with methanesulfonic acid in methanol to give 12. Similarly, 13 and 14 were made from the corresponding benzyl chlorides. Compound 15 was prepared by the click reaction under the same condition as for 10 using 2-fluoroethylazide and 13. The mesylate precursor 16 for the labeling of 12 with $^{18}$F was synthesized by reflux of 14 and silver methanesulfonate in acetonitrile.

Scheme 1. Synthesis of derivatives of NU1085 (2)

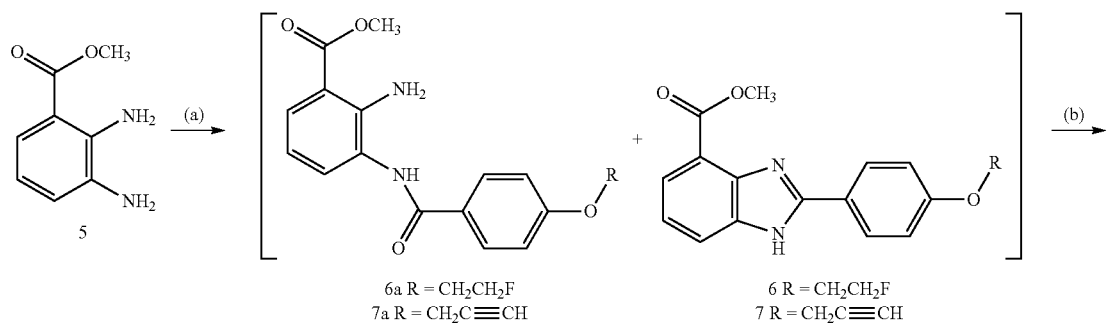

6a R = CH$_2$CH$_2$F
7a R = CH$_2$C≡CH

6 R = CH$_2$CH$_2$F
7 R = CH$_2$C≡CH

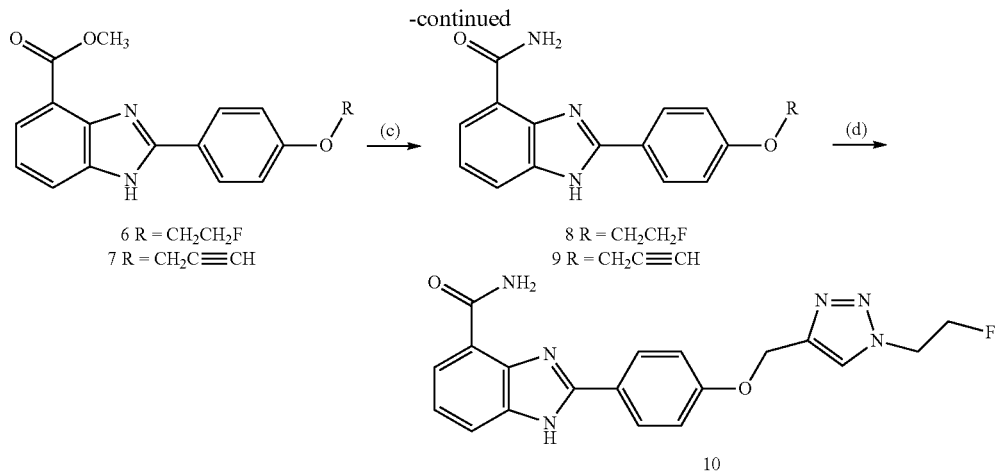

Reagents and conditions: (a) ROC₆H₄COCl (R = CH₂CH₂F for 6a and 6, R = CH₂C≡CH for 7a and 7) pyridine, CH₂Cl₂; (b) CH₃SO₃H, MeOH; (c) NH₃, MeOH; (d) 9, FCH₂CH₂N₃, CuSO₄, sodium ascorbate, DMF.

Scheme 2. Synthesis of derivatives of AG014361 (3)

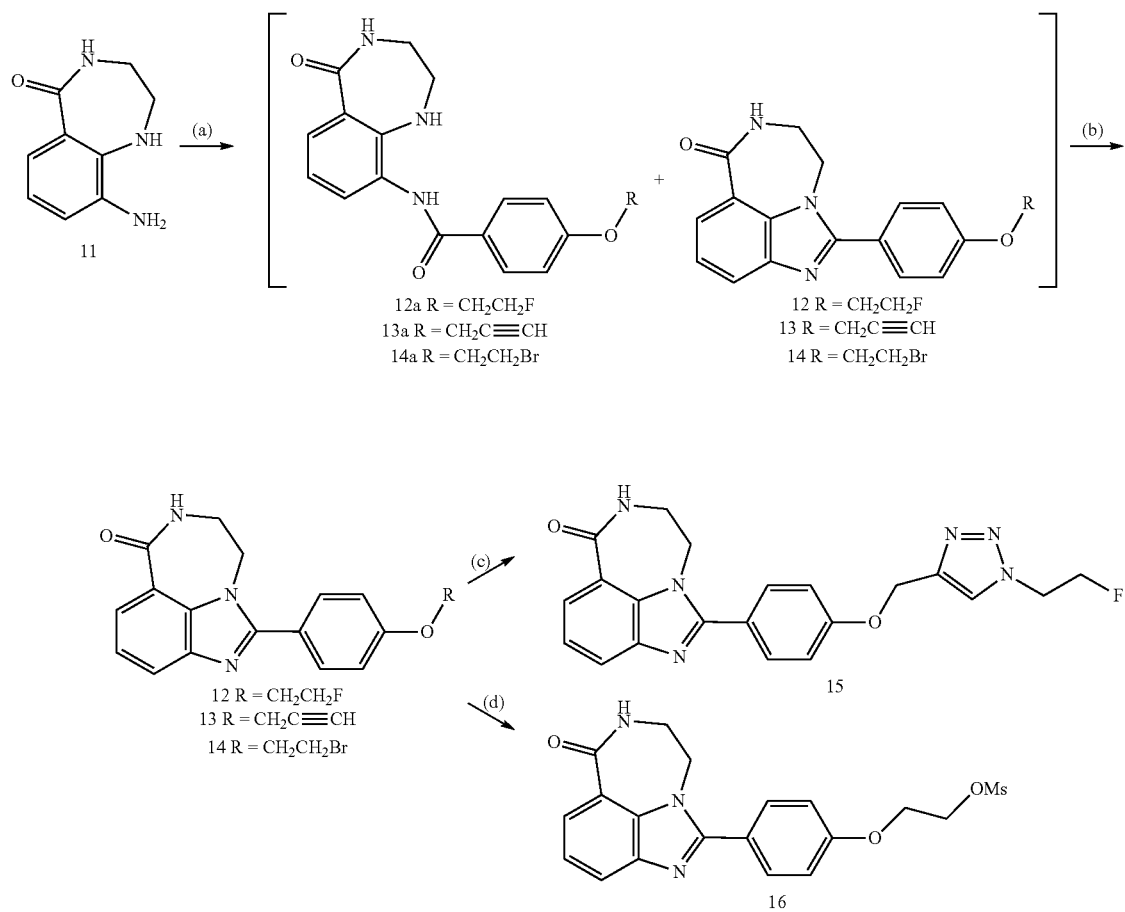

Reagents and conditions: (a) ROC₆H₄COCl (R = CH₂CH₂F for 12a and 12, R = CH₂C≡CH for 13a and 13, R = CH₂CH₂Br for 14a and 14), pyridine, CH₂Cl₂; (b) CH₃SO₃H, MeOH; (c) 13, FCH₂CH₂N₃, CuSO₄, sodium ascorbate, DMF; (d) 14, AgOMs, acetonitrile.

Example 2

This example illustrates the synthesis of Methyl 2-(4-(2-fluoroethoxy)phenyl)-1H-benzo[d]imidazole-4-carboxylate (6). Compound numbers refer to Schemes 1 and 2, supra.

A mixture of methyl 2,3-diaminobenzoate 5 (500 mg, 3 mmol) and 4-(2-fluoroethoxy)benzoyl chloride (638 mg, 3.15 mmol) in $CH_2Cl_2$ (10 mL) and pyridine (10 mL) was stirred overnight at 23° C., After removal of the solvent under reduced pressure, the residue was dissolved in methanol (50 mL), and followed by addition of $CH_3SO_3H$ (1 mL). After the mixture was refluxed for 3 h, methanol was removed under reduced pressure, and the residue was dissolved in ethyl acetate (75 mL). The solution was washed with saturated $Na_2CO_3$ (50 mL), water (50 mL) and saturated NaCl (50 mL), and dried over $Na_2SO_4$. After evaporation of the solvent, the crude product was purified by silica gel column chromatography eluting with hexane-ethyl acetate (1:1) to afford 6 as white solid (686 mg, 73%), mp 134.2-134.6° C. $^1H$ NMR (300 MHz, $CDCl_3$) δ 10.58 (s, 1H), 7.98 (d, J=8.7 Hz, 2H), 7.95 (d, J=8.7 Hz, 1H), 7.83 (d, J=7.2 Hz, 1H), 7.26 (t, J=7.8 Hz, 1H), 6.98 (d, J=9.0 Hz, 2H), 4.75 (dt, J=47.1 Hz, 4.2 Hz, 2H), 4.22 (dt, J=27.6 Hz, 4.2 Hz, 2H), 3.96 (s, 3H). $^{13}C$ NMR (75 MHz, $CDCl_3$) δ 167.0, 160.2, 152.3, 144.8, 135.0, 128.2, 124.4, 124.2, 122.3, 121.7, 114.9, 113.0, 81.6 (d, J=169.7 Hz), 67.1 (d, J=20.6 Hz), 52.0.

Example 3

This example illustrates the synthesis of Methyl 2-(4-(prop-2-ynyloxy)phenyl)-1H-benzo[d]imidazole-d-carboxylate (7). Compound numbers refer to Schemes 1 and 2, supra.

Compound 7 was prepared according to the same procedure for compound 6 (Example 2), except using compound 5 (500 mg, 3 mmol) and 4-(prop-2-ynyloxy)benzoyl chloride (613 mg, 3.15 mmol) as starting materials. The crude product was purified by silica gel column chromatography eluting with hexane-ethyl acetate (1:1) to afford 7 as white solid (724 mg, 79%), mp 176.0-176.8° C. $^1H$ NMR (300 MHz, $CDCl_3$) δ 10.58, 8.03 (d, J=9.0 Hz. 2H), 7.98 (d, J=8.1 Hz, 1H), 7.86 (d, J=7.8 Hz, 1H), 7.29 (t, J=8.1 Hz, 1H), 7.10 (d, J=9.0 Hz, 2H), 4.76 (d, J=2.4 Hz, 2H), 4.00 (s, 3H), 2.57 (t J=2.4 Hz, 1H), $^{13}C$ NMR (75 MHz, $CDCl_3$) δ 167.1, 159.4, 152.4, 144.9, 135.1, 128.2, 124.6, 124.3, 122.8, 121.8, 115.4, 113.0, 77.9, 76.0, 55.8, 52.1.

Example 4

This example illustrates the synthesis of 2-(4-(2-Fluoroethoxy)phenyl)-1H-benzo[d]imidazole-4-carboxamide (8). Compound numbers refer to Schemes 1 and 2, supra.

A solution of Compound 6 (315 mg, 1 mmol) in 7 N $NH_3$ in methanol (10 mL) was stirred for 3 days at 23° C. After evaporation of the solvent, the crude product was purified by silica gel column chromatography eluting with hexane-ethyl acetate (1:2) to afford 8 as white solid (245 mg, 82%), mp 195.8-197.4° C. $^1H$ NMR (300 MHz, DMSO-$d_6$) δ 9.44 (s, 1H), 8.23 (d, J=9.0 Hz, 2H), 7.89 (d, J=7.5 Hz, 1H), 7.80 (s, 2H), 7.74 (d, J=7.8 Hz, 1H), 7.34 (t, J=7.5 Hz, 1H), 7.20 (d, J=8.4 Hz, 2H), 4.81 (dt, J=47.7 Hz, 3.6 Hz, 2H), 4.37 (dt, J=30.0 Hz, 3.9 Hz, 2H). $^{13}C$ NMR (75 MHz, DMSO-$d_6$) δ 166.4, 160.1, 152.0, 135.5, 128.6, 122.7, 122.0, 115.1, 82.1 (d, J=166.2 Hz), 67.3 (d, J=19.4 Hz). Anal. Calcd for $C_{16}H_{14}FN_3O_2.0.5H_2O$: C, 62.33; H, 4.90; N, 13.63. Found: C. 62.54; H, 4.87; N, 13.67.

Example 5

This example illustrates the synthesis of 2-(4-(Prop-2-ynyloxy)phenyl)-1H-benzo[d]imidazole-4-carboxamide (9). Compound numbers refer to Schemes 1 and 2, supra.

Compound 9 was prepared according to the same procedure for compound 8, except using compound 7 (460 mg, 1.5 mmol) as starting material. The crude product was purified by silica gel column chromatography eluting with hexane-ethyl acetate (1:2) to afford 9 as white solid (378 mg, 86%), mp 183.4-183.9° C. $^1H$ NMR (300 MHz, DMSO-$d_6$) δ 9.39 (s, 1H), 8.21 (d, J=8.4 Hz, 2H). 7.87 (d, J=7.8 Hz, 1H), 7.78 (s, 2H), 7.72 (d, J=7.8 Hz, 1H), 7.32 (t, J=7.8 Hz, 1H), 7.20 (d, J=9.0 Hz, 2H) 4.92 (d, J=1.8 Hz, 2H), 3.63 (s, 1H). $^{13}C$ NMR (75 MHz, DMSO-$d_6$) δ 166.4, 159.0, 152.0, 128.5, 122.7, 122.3, 121.9, 115.4, 78.9, 78.6, 55.7. Anal. Calcd for $C_{17}H_{18}N_3O_2.0.5H_2O$: C, 67.99; H, 4.70; N, 13.99. Found: C, 67.97; H, 4.72; N, 13.71.

Example 6

This example illustrates the synthesis of 2-(4-((1-(2-Fluoroethyl)-1H-1,2,3-triazol-4-yl)methoxy)phenyl)-1H-benzo[d]imidazole-4-carboxamide (10). Compound numbers refer to Schemes 1 and 2 supra.

A mixture of 9 (291 mg, 1.0 mmol). 1-azido-2-fluoroethane (1.68 mmol), sodium ascorbate (990 mg, 5.0 mmol), and $CuSO_4.5H_2O$ (125 mg, 0.5 mmol) in DMF (10 ml) was stirred overnight at 23° C. The reaction mixture was diluted with ethyl acetate (75 mL), and washed with water (2×50 mL), and saturated NaCl (50 mL), dried over $Na_2SO_4$. After evaporation of the solvent, the crude product was purified by silica gel column chromatography eluting with ethyl acetate to afford 10 as white solid (255 mg, 67%) mp 256.4-257.3° C. $^1H$ NMR (300 MHz, DMSO-$d_6$) δ 9.42 (s, 1H), 8.33 (s, 1H), 8.21 (d, J=8.7 Hz, 2H), 7.87 (d, J=7.5 Hz, 1H), 7.78 (s, 2H), 7.71 (d, J=7.8 Hz, 1H), 7.32 (t, J=7.8 Hz, 1H), 7.27 (d, J=8.7 Hz, 2H), 5.28 (s, 2H), 4.85 (dt, J=46.8 Hz, 4.5 Hz, 2H), 4.76 (dt, J=27.6 Hz, 4.2 Hz, 2H). $^{13}C$ NMR (75 MHz, DMSO-$d_6$) δ 166.3, 159.9, 152.0, 142.5, 142.5, 141.6, 135.3, 128.6, 125.1, 122.7, 122.1, 121.9, 115.3, 114.7, 99.5, 81.9 (d, J=167.3 Hz), 61.3, 50.1 (d, J=20.5 Hz). Anal. Calcd for $C_{19}H_{17}FN_6O_2$: C, 59.99; H, 4.50; N, 22.09. Found: C, 60.10; H, 4.67; N, 21.49.

Example 7

This example illustrates the synthesis of 5,6-Dihydro-2-(4-(2-fluoroethoxy)phenyl)-imidazo [4,5,1-jk][1,4]benezodiazepin-7(4H)-one (12). Compound numbers refer to Schemes 1 and 2, supra.

Compound 12 (WC-4-138) was prepared according to the same procedure for compound 6, except using compound 11 (177 mg, 1 mmol) and 4-(2-fluoroethoxy)benzoyl chloride (213 mg, 1.05 mmol) as starling materials. The crude product was purified by silica gel column chromatography eluting with ethyl acetate-methanol (10:1) to afford 12 as white solid (247 mg, 76%), mp 236.0-237.5° C. $^1H$ NMR (300 MHz/DMSO-$d_6$) δ 8.44 (t, J=5.1 Hz, 1H), 7.89-7.80 (m, 4H), 7.34 (d, J=7.9 Hz, 1H), 7.17 (d, J=8.7 Hz, 2H), 4.79 (dt, J=48.9 Hz, 3.6 Hz, 2H), 4.44 (m, 2H), 4.35 (dt, J=31.2 Hz, 3.9 Hz, 2H), 3.53 (m, 2H). $^{13}C$ NMR (75 MHz, DMSO-$d_6$) δ 167.8, 159.9, 154.1, 143.7, 132.9, 131.7, 125.5, 123.1, 122.5, 121.9, 118.1, 115.1, 82.5 (d, J=165.0 Hz), 67.7 (d, J=19.3 Hz), 50.9, 40.8. Anal. Calcd for $C_{18}H_{16}FN_3O_3$: C, 66.45; H, 4.96; N, 12.92. Found; C, 66.43; H, 5.03; N, 12.92.

Example 8

This example illustrates the synthesis of 5,6-Dihydro-2-(4-(prop-2-ynyloxy)phenyl)-imidazo[4,5,1-jk][1,4]benzodiazepine-7(4H)-one (13). Compound numbers refer to Schemes 1 and 2, supra.

Compound 13 was prepared according to the same procedure for compound 6, except using, compound 11 (177 mg, 1 mmol) and 4-(prop-2-ynyloxy)benzoyl chloride (204 mg, 1.05 mmol) as starting materials. The crude product was purified by silica gel column chromatography eluting with ethyl acetate-methanol (10:1) to afford 13 as white solid (268 mg, 84%), mp 258.0-259.1° C. $^1$H NMR (300 MHz, DMSO-d$_6$) δ 8.47 (s, 1H), 7.85 (m, 4H), 7.34 (t, J=7.8 Hz, 1H), 7.18 (d, J=6.9 Hz, 2H), 4.93 (s, 2H), 4.46 (m, 2H), 3.64 (s, 1H), 3.54 (m, 2H), $^{13}$C NMR (75 MHz, DMSO-d$_6$) δ 167.4, 158.5, 153.6, 143.3, 132.5, 131.1, 125.1, 122.7, 122.4, 121.5, 117.7, 115.0, 79.0, 78.5, 55.6, 50.5. Anal. Calcd for C$_{19}$H$_{15}$N$_3$O$_2$: C, 71.91; H, 4.76; N, 13.24. Found: C, 71.71; H, 4.82; N, 12.98.

Example 9

This example illustrates the synthesis of 2-(4-(2-Bromoethoxy)phenyl)-5,6-dihydro-imidazo[4,5,1-jk][1,4]benzodiazepin-7(4H)-one (14). Compound numbers refer to Schemes 1 and 2, supra.

Compound 14 was prepared according to the same procedure for compound 6, except using compound 11 (177 mg, 1 mmol) and 4-(2-bromoethoxy)benzoyl chloride (277 mg, 1.05 mmol) as starting materials. The crude product was purified by silica gel column chromatography eluting with ethyl acetate-methanol (10:1) to afford 14 as white solid (255 mg, 66%), mp decomposed 280° C. $^1$H NMR (400 MHz, DMSO-d$_6$) δ 8.44 (t, J=5.6 Hz, 1H), 7.87 (d, J=8.0 Hz, 1H), 7.85 (d, J=8.0 Hz, 1H), 7.82 (d, J=8.4 Hz, 2H), 7.34 (t, J=7.6 Hz, 1H), 7.16 (d, J=8.4 Hz, 2H), 4.44 (m, 4H), 3.86 (t, J=5.2 Hz, 2H), 3.53 (m, 2H). $^{13}$C NMR (100 MHz, DMSO-d$_6$) δ 167.8, 159.7, 154.1, 143.7, 132.9, 131.7, 125.5, 123.1, 122.6, 122.0, 118.1, 115.2, 68.4, 50.5, 40.8.

Example 10

This example illustrates the synthesis of 5,6-Dihydro-2-(4-((1-(2-fluoroethyl)-1H-1,2,3-triazol-4-yl)methoxy)phenyl)-imidazo[4,5,1-jk][1,4]benzodiazepin-7(4H)-one (15). Compound numbers refer to Schemes 1 and 2, supra.

Compound 15 was prepared according to the same procedure for compound 10, except using compound 13 (159 mg, 0.5 mmol) as starting material. The crude product was purified by silica gel column chromatography eluting with ethyl acetate-methanol (10:1) to afford 15 as white solid (147 mg, 72%), mp 226.5-227.6° C. $^1$H NMR (300 MHz, DMSO-d$_6$) δ 8.46 (t, J=5.7 Hz, 1H), 8.33 (s, 1H), 7.8-7.81 (m, 4H), 7.34 (t, J=7.8 Hz, 1H), 7.25 (d, J=8.4 Hz, 2H), 5.28 (s, 2H), 4.85 (dt. J=47.1 Hz, 4.2 Hz, 2H), 4.76 (dt. J=27.6 Hz, 4.2 Hz, 2H), 4.45 (m, 2H), 3.54 (m, 2H). $^{13}$C NMR (75 MHz, DMSO-d$_6$) δ 167.4, 159.4, 143.3, 142.6, 131.2, 125.1, 125.0, 122.7, 122.0, 121.5, 117.7, 114.8, 81.9 (d, J=167.3 Hz), 61.2, 50.5, 50.1 (d, J=20.5 Hz), 40.4. Anal. Calcd for C$_{21}$H$_{19}$FN$_6$O$_2$·1.5H$_2$O: C, 58.19; H, 5.12; N, 19.39. Found: C, 57.89; H, 4.54; N, 18.92.

Example 11

This example illustrates the synthesis of 5,6-Dihydro-2-(4-(2-(methylsulfonyloxy)ethoxy)phenyl)-imidazo[4,5,1-jk][1,4]benzodiazepin-7(4H)-one (16). Compound numbers refer to Schemes 1 and 2, supra.

A mixture of 14 (193 mg, 0.5 mmol) and AgOMs (508 mg, 2.5 mmol) was refluxed for 8 h. After evaporation of the solvent, the crude product was purified by silica gel column chromatography eluting with ethyl acetate-methanol (10:1) to afford 16 as white solid (129 mg, 64%), mp 253.2-254.1° C. $^1$H NMR (400 MHz, CD$_3$OD) δ 7.97 (d, J=8.0 Hz, 1H), 7.88 (d, J=8.0 Hz, 1H), 7.76 (d, J=8.8 Hz, 2H), 7.40 (t, J=8.0 Hz, 1H), 7.17 (d, J=8.8 Hz, 2H), 4.59 (t, J=4.0 Hz, 2H), 4.49 (t, J=4.0 Hz, 2H), 4.35 (t, J=4.0 Hz, 2H), 3.65 (m, 2H), 3.12 (s, 3H). $^{13}$C NMR (100 MHz, CD$_3$OD) δ 160.2, 148.1, 142.7, 135.7, 132.2, 131.1, 131.0, 125.8, 122.6, 122.1, 121.4, 116.9, 114.6, 68.3, 66.0, 50.5, 40.6, 36.0.

Example 12

This example illustrates PARP-1 activity assays.

Newly synthesized PARP-1 inhibitors were assessed for their ability to inhibit active PARP-1 using the method described by Putt and Hergenrother.[23] The results are shown in Table 1. The tricycle benzimidazole compounds had higher inhibition potency than their respective benzimidazole analogs (e.g., 12 vs. 8, 15 vs. 10). In both benzimidazole and tricycle benzimidazole analogs, the analogs with fluoroethoxy substituent had three times higher inhibition potencies than the respective analogs with fluoroethyl triazole group (e.g., 8 vs. 10, 12 vs. 15). Therefore, the most potent inhibitor, 12, was selected for $^{18}$F-labeling.

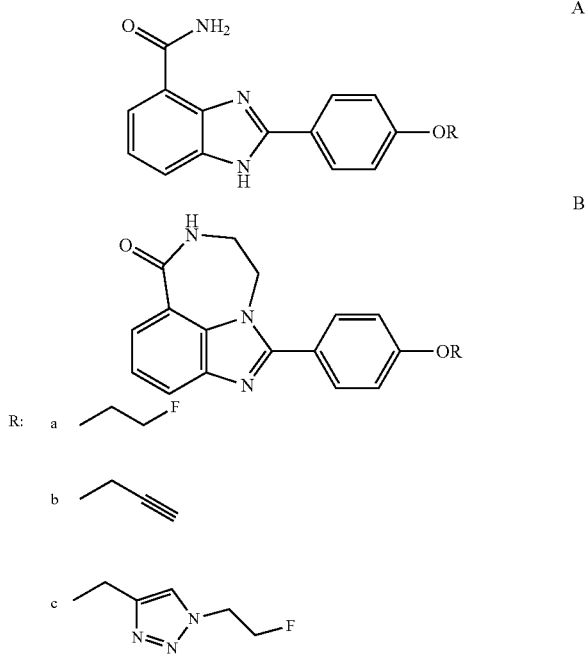

TABLE 1

| Inhibition efficiency of PARP-1 inhibitors | | | |
|---|---|---|---|
| Compound | Structure | R | IC$_{50}$ (nM) |
| 1 PJ34 | / | / | 170.2 ± 8.3$^a$ |
| 8 | A | a | 10.8 ± 0.4 |
| 9 | A | b | 25.8 ± 3.3 |

TABLE 1-continued

Inhibition efficiency of PARP-1 inhibitors

| Compound | Structure | R | IC$_{50}$ (nM) |
|---|---|---|---|
| 10 | A | c | 30.3 ± 5.6 |
| 12 | B | a | 6.3 ± 1.3 |
| 13 | B | b | 18.7 ± 2.7 |
| 15 | B | c | 22.1 ± 6.3 |

[a]Reported values: IC$_{50}$ = 20 nM, EC$_{50}$ = 35 nm;[3,24]

Example 13

This example illustrates a PARP-1 enzymatic activity assay.

This assay is based on the chemical quantification of NAD$^+$, i.e. the amount of NAD$^+$ consumed when the active PARP-1 C-terminal catalytic domain sequentially transfers ADP-ribose subunits from nicotinamide adenine dinucleotide (NAD$^+$) to protein acceptors.[7]

High-specific-activity PARP-1 and activated DNA were purchased from Trevigen (Gaithersburg, Md.). All other reagents required for this assay including NAD$^+$ were purchased from Sigma-Aldrich (St. Louis, Mo.). Known PARP-1 inhibitor PJ-34, used as a control in these experiments, was synthesized in-house. To test the compounds for PARP-1 inhibition, a solution of 250 nM NAD$^+$ was first made in 50 mM Tris-HCl. 2 mM MgCl$_2$, at pH 8.0 PARP assay buffer) and 20 µL transferred to each well of a 96-well black fluorescence plate. A solution of 50 µg/mL of activated DNA was made in PARP assay buffer and 10 µL was added to each well. Stock solutions of test compounds were first prepared in DMSO, diluted to varying concentrations in PARP assay buffer, and 10 µL was added to each well. To initiate the reaction, 10 µL of 10 µg/mL PARP-1 enzyme in PARP assay buffer was added to each well. The total volume was 50 µL, bringing the final concentrations to 2 µg/mL PARP-1 enzyme, 10 µg mL activated DNA, and 100 nM NAD$^+$ per well. The plate was then incubated at room temperature for 20 min. The amount of NAD$^+$ present was then determined by first adding 20 µL 2 M KOH, followed by 20 µL of 20% acetophenone (in ethanol) to each well. The plate was allowed to incubate at 4° C. for 10 min. Then 90 µL of 88% formic acid was added, resulting in a final concentration of 222 mM KOH, 2.2% acetophenone, 44% formic acid, and varying concentrations of NAD$^+$. The plate was incubated at 100° C. for 5 min., allowed to cool, and then, read on a Perkin Elmer Victor microplate fluorometer (Waltham, Mass.) using 360 nm excitation and 450 nm emission filters. Dose-response curves were generated using GraphPad Prism version 5.04 for Windows (San Diego, Calif.) where control wells containing NAD$^+$ only were set at 0% PARP activity and control wells containing PARP-1 only were set at 100% PARP activity. IC$_{50}$ values were calculated from the dose-response curves generated from at least three independent experiments and reported in Table 1 as mean±standard deviation (SD).

Example 14

This example illustrates the synthesis of radio-labeled PARP-1 inhibitors.

Figure 2:
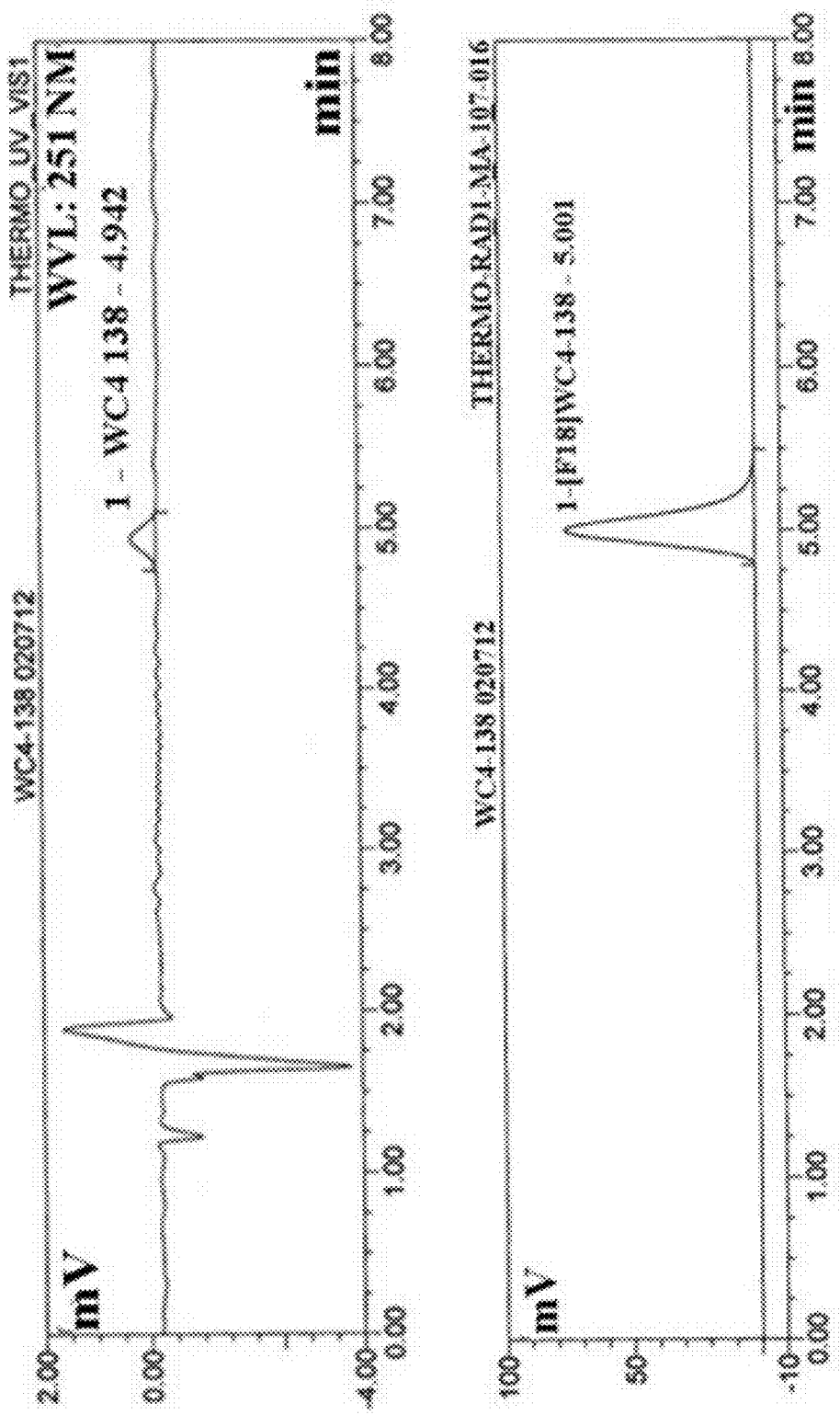
FIG. 2 illustrates analytical HPLC of [$^{18}$F]12 (WC-4-138), showing high chemical and radiochemical purities. (Top: UV, Bottom: radioactivity: specific activity=11,500 mCi/µmol).

[$^{18}$F]12 was synthesized by the nucleophilic substitution of the mesylate precursor 16 under conventional conditions (K$_{222}$/K$_2$CO$_3$) in DMF at 105° C. (Scheme 3), affording [$^{18}$F]12 in 40-50% yield (decay corrected) after reversed phase HPLC purification and solid phase extraction (FIG. 2). The total synthesis time was 90 min. The specific activity of the final dose in 10% ethanol/saline was 5500-18000 mCi/µmol.

Scheme 3. Radiosynthesis of [$^{18}$F]12

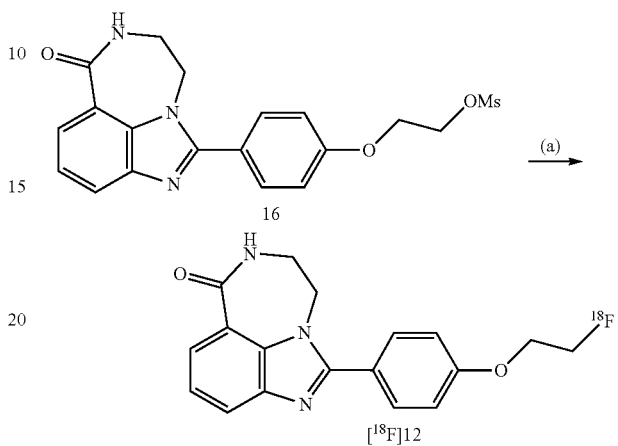

Reagents and conditions: [$^{18}$F]KF, K$_{222}$, K$_2$CO$_3$, DMF, 105° C., 10 min.

Example 15

This example further illustrates the synthesis [$^{18}$F]Compound 12 (WC-4-138).

[$^{18}$F]fluoride (up to 50 mCi in 100-500 µL [$^{18}$O]water) was transferred to a BD vacutainer (13×75 mm, 5 mL, glass, no additives) containing K$_{222}$ (2.2 mg, 5.8 µmol) and K$_2$CO$_3$ (0.3 mg. 2.2 µmol). The mixture was then dried by azeotropic distillation at 105° C. using acetonitrile (3×1 mL) under a gentle flow of N$_2$ gas. When the drying was nearly finished, the vacutainer was removed from the oil bath and the solvent residue (100 µL) was removed by a flow of N$_2$ at room temperature. A solution of 16 (0.65 mg. 1.6 µmol) in DMF (300 µL) was added to the vacutainer and then shaken and heated at 105° C. for 10 min. At room temperature, the reaction mixture was diluted with water (2 mL) and then loaded onto a semi-preparative column (A) for purification (18% acetonitrile/82% water/0.1% TFA, 4 mL/min, 251 nm). The HPLC fraction containing [$^{18}$F]12 was collected, and [$^{18}$F]12 was obtained in ethanol using standard solid phase extraction method. The dose was diluted to 10% ethanol in saline. An analytical column (B) was used to analyze the dose (32% acetonitrile/68% 0.1 M ammonium formate buffer pH=4.5, 2 mL/min, 251 nm). The total synthesis time was 90 min, the decay corrected yields 40-50%, the radiochemical purity 100%, and the specific activity ranged from 5500 to 18000 mCi/µmol at the end of synthesis.

Example 16

Figure 3A:
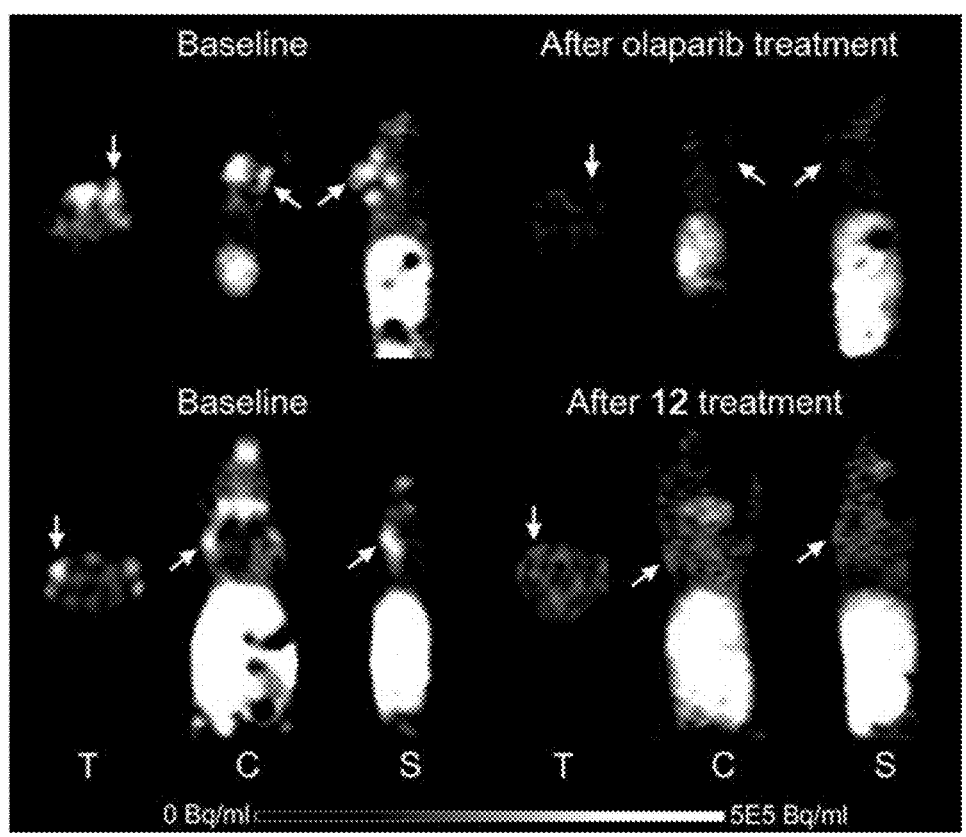
FIG. 3A-D illustrate microPET images of MDA-MB-231 and MDA-MB-436 tumors in mice at 60 min using [$^{18}$F]12 under baseline conditions and blocked with olaparib (i.p. 50 mg/kg 20 min pretreatment) and 12 (i.p. 1 mg/kg 20 min pretreatment).
Figure 3B:
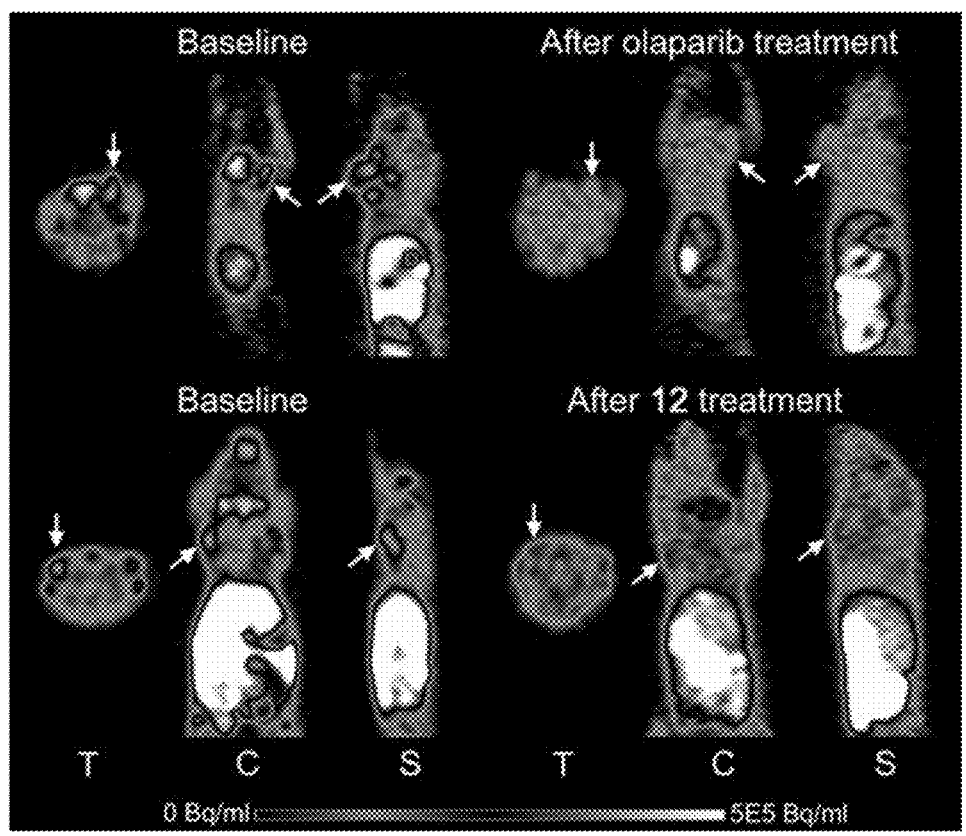
Figure 3C:
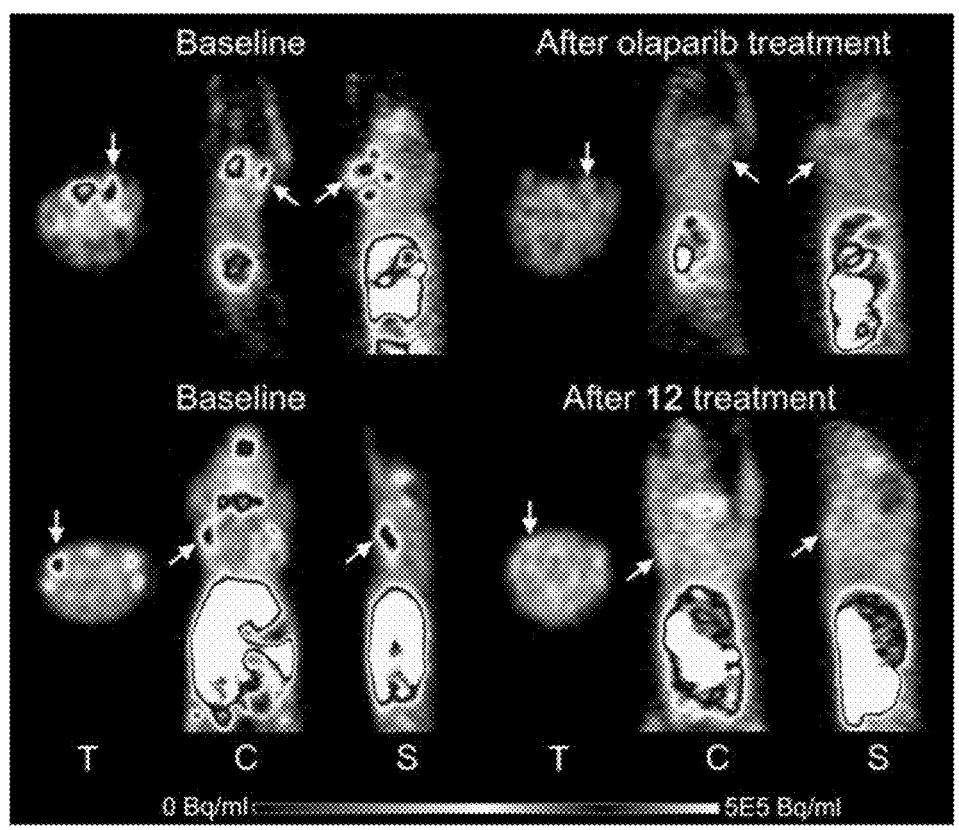
Figure 3D:
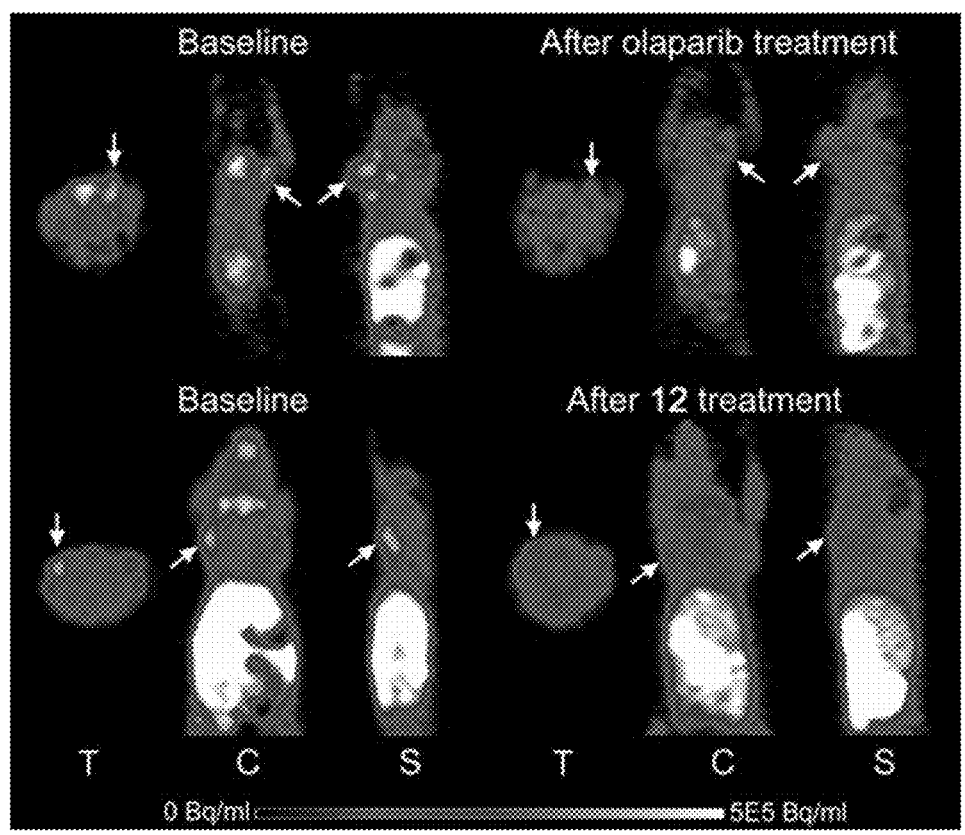

This example illustrates the visualization of tumor tissue in microPET in mice. MDA-MB-436 human breast cancer xenograft tumors in immune-deficient mice were visualized by PET using [$^{18}$F]12. These tumors demonstrated increased uptake that was distinguishable from background at 60 min post-tracer injection (FIG. 3). The same mice treated with olaparib (50 mg/kg i.p.) or 12 (1 mg/kg i.p.) 20 min prior to tracer injection decreased [$^{18}$F]12 uptake in the tumors to the background tissue activity levels (FIG. 3). In FIG. 3A-D the top row displays an MDA-MB-231 tumor before and after treatment with olaparib (i.p. 50 mg/kg 20 min pretreatment, and the bottom row displays MDA-MB-436 (right) and MDA-MB-231 (left) tumors before and after 12 (i.p. 1 mg/kg 20 min pretreatment). FIG. 3A, FIG. 3B and FIG. 3C represent red, green, and blue RGB channels, respectively, each rendered in black-and-white. FIG. 3D represents a composite of RGB channels rendered in black-and-white.

Figure 4:
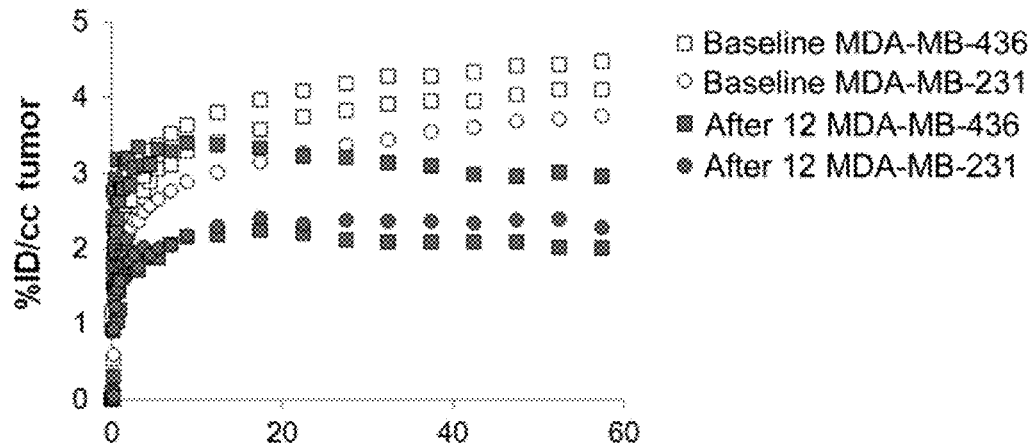
FIG. 4 illustrates time-radioactivity curve of [$^{18}$F]12 in MDA-MB-436 tumors in mice under baseline conditions and blocked with olaparib (i.p. 50 mg/kg 20 min pretreatment) and 12 (i.p. 1 mg/kg 20 min pretreatment, top graph). The olaparib treated MDA-MB-231 tumor also demonstrated decreased [$^{18}$F]12 uptake (bottom graph).
Figure 4:
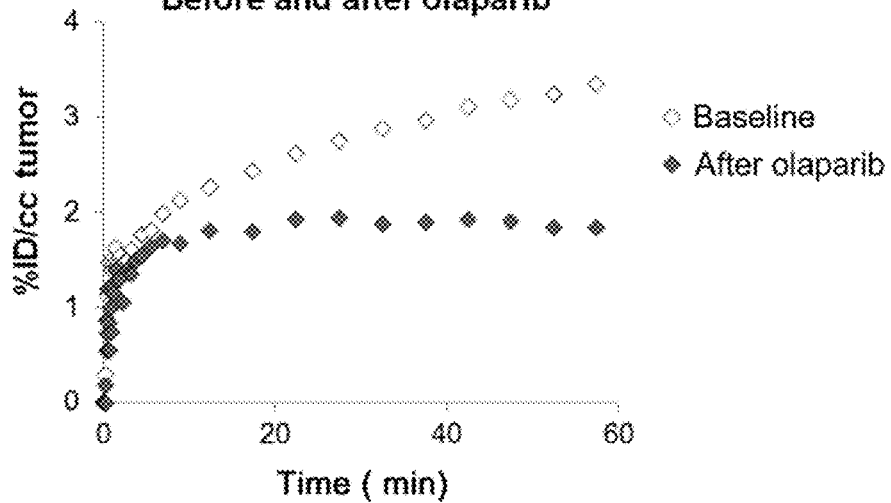

The time-radioactivity curves of [$^{18}$F]12 in the tumors from 0-60 min of the microPET studies confirmed the visual assessment of the microPET images (FIG. 4), demonstrating significantly decreased [$^{18}$F]12 uptake as a result of treatment with either olaparib or 12.

MDA-MB-436 is a human breast cancer cell line with innately high levels of PARP-1 activity[19] and has been used in a mouse models to assess the efficacy of the $^{18}$F-labeled olaparib derivative for imaging PARP-1 activity with micro PET. [$^{18}$F]12 progressively accumulated in the tumor during the 1 hour microPFT acquisition, and [$^{18}$F]12 uptake was blocked in animals pretreated with either olaparib or 12. Both olaparib and 12 are competitive PARP-1 inhibitors with high inhibition potencies ($IC_{50}$=5 nM[31] and 6.3 nM, respectively). Thus, our data indicate that [$^{18}$F]12 uptake in the mouse model is due to PARP-1 expression, and that [$^{18}$F]12 is an effective PET tracer for in vivo imaging of PARP-1 expression specifically.

Example 17

This example illustrates the visualization of tumor tissue in mice using PET.

MDA-MB-436 and MDA-MB-231 human breast cancer cells were maintained in cell culture under standard conditions with 5% $CO_2$ atmosphere using Eagle's minimum essential medium (with Earle's balanced salt solution and 2 mM L-glutamine) supplemented with 2 mM E-glutamine, 1 mM sodium pyruvate, 0.1 mM non-essential amino acids 2% vitamins for MEM, and 5% fetal bovine serum. Cells in exponential growth were trypsinized and harvested for tumor implantation. After counting, cells were re-suspended in ice-cold 1:1 Matrigel and PBS to give the desired concentration and held on ice.

Mature female athymic nu/nu mice from Charles River Laboratories are allowed to acclimate in an AALAC accredited housing facility for at least 1 week prior to tumor implantation for these serial imaging studies. Female nu/nu mice were implanted in the mammary fat pads (near the auxiliary lymph nodes) with ~8×10$^6$ MDA-MB-436 breast cancer cells in ~100 µL of 1:1 Matrigel:PBS. Imaging studies were conducted 2-3 weeks post implantation.

Tumor-bearing mice were placed in an induction chamber containing ~2% isoflurane/oxygen and then secured to a custom double bed for placement of tail vein catheters; anesthesia was maintained via nose-cone at ~1% isoflurane/oxygen for the dynamic imaging procedure. The mice were injected with 150-200 µCi of [$^{18}$F]12 and scanned for 0-60 min using Focus 220 and Inveon PET/CT scanners. The standard uptake values (SUVs) were generated from manually drawn regions of interests for tumors and surrounding 'background' tissue. Visualization of specific uptake was determined by comparison of baseline scans with images acquired by tracer injection 20 minutes after pre-treatment with the blocking agents olaparib (50 mg/kg, IP) or 12 (1 mg/kg, IP).

Example 18

This example illustrates the uptake of [$^{18}$F]WC-4-138 (Compound 12) in cell culture assays.

In these experiments, the head and neck squamous cell carcinoma lines SCC1, SCC15, and SCC25 (ATCC) were propagated in Dulbecco's Modified Eagle's Medium (DMEM, Gibco) supplemented with 10% Fetal Bovine Serum (FBS, Gibco), Penicillin-Streptomycin (P/S, Gibco), and 100 ng/ml hydrocortisone (Sigma-Aldrich). The small cell lung cancer lines NCI-h69 and NCI-h82 (ATCC) were propagated m RPMI Medium (Gibco) supplemented with 10% FBS and 1% P/S. The human breast cancer cell line MDA-MB-231 (ATCC) was propagated in Eagle's Minimum Essential Medium (Gibco) supplemented with 5% FBS, 2% Vitamins for MEM (Gibco), 1% 200 mM L-glutamine (Gibco), 1% 10 mM Non-Essential Amino Acid (NEAA, Gibco).

For each experimental replicate, approximately 1 µCi of [$^{18}$F]WC-4-138 was diluted in 1 ml of cell culture medium and added to 10$^6$ cells. After 5, 30, or 60 minutes, the medium was collected and cells were washed twice in 0.7 ml Phosphate Buffered Saline (PBS, Gibco). Adherent cells were collected by scraping the cell culture dish and transferring to a microfuge tube. Radioactivity was measured in the collected medium, PBS, or cell pellets. Protein from the cell pellet was quantified using a standard chemiluminescent PARP ELISA kit (Trevigen #4520-096-K). All data were decay-corrected and normalized to total protein quantity in the cell pellet. For drug treatment studies, cells were incubated with 10 µM Olaparib or Iniparib twenty-hours prior to incubation with [$^{18}$F]WC-4-138.

Figure 5A:
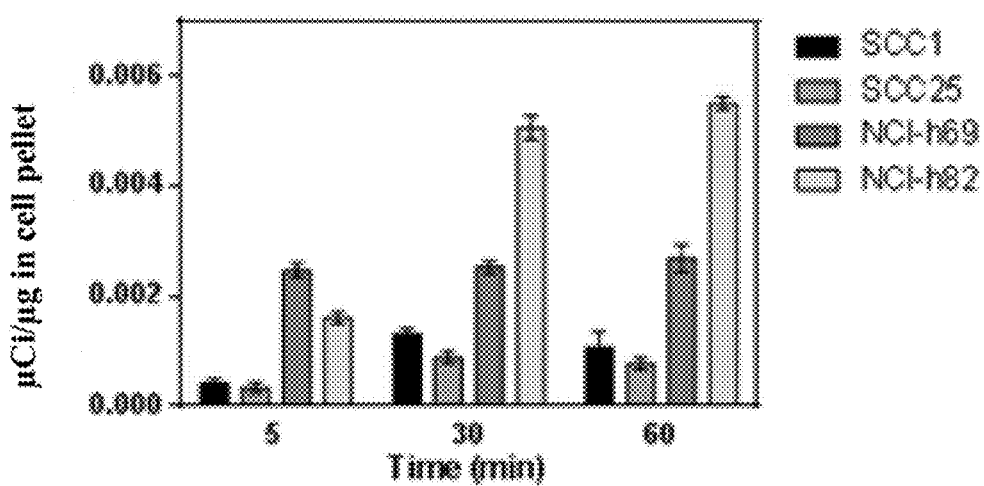
FIG. 5A-D illustrates analysis of [$^{18}$F]WC-4-138 (12) uptake and PARP activity in cancer cell lines.
Figure 5B:
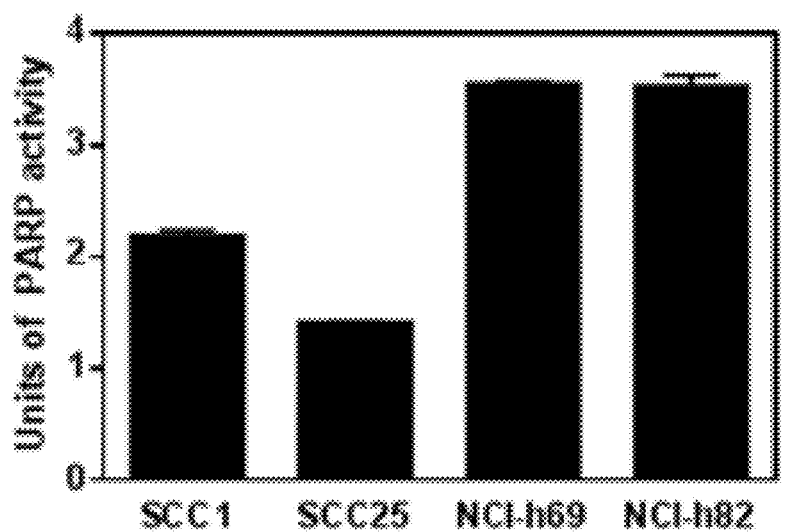
Figure 5C:
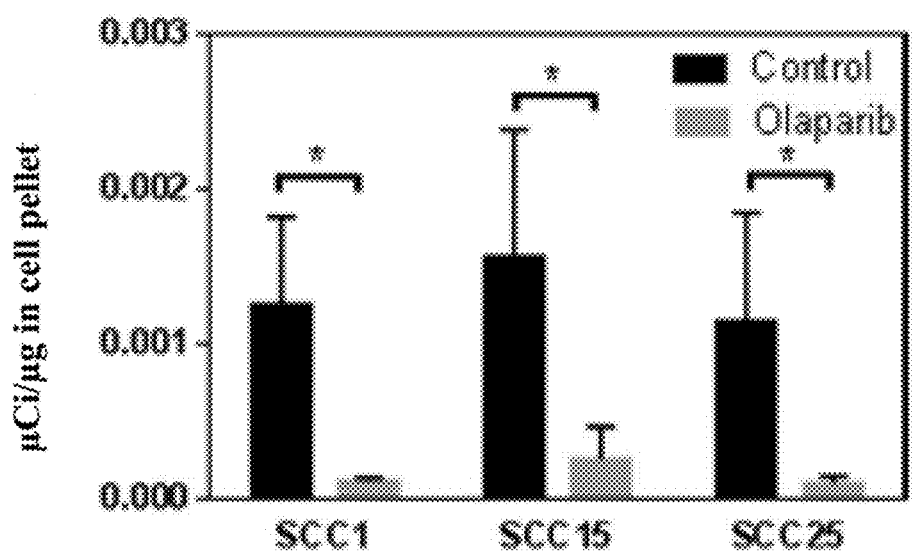

The head and neck cell lines SCC1 and SCC25 constitutively take up small amounts of tracer, registering as 0.001-0.002 µCi/µg in the cell pellet (FIG. 5A). Lung cell lines NCI-h69 and NCI-h82 take up [$^{18}$F]WC-4-138 registering 0.004-0.006 µCi/µg in the cell pellet (FIG. 5A). Radioactivity was measured in head and neck squamous cell cancer (HNSCC) lines (SCC1 and SCC25) or small cell lung cancer (SCLC) lines (NCI-h69 and NCI-h82) after incubation with [$^{18}$F]WC-4-138 for 5, 30, or 60 minutes (n=3 at each time point). These figures represent 1-2 units of PARP activity for the SCC cells and about 3.5 units of Parp activity for the NCI cells (FIG. 5B). PARP activity was measured in HNSCC or lung SCLC cells. (FIG. 5C-D) [$^{18}$F]WC-4-138 uptake was measured in HNSCC cell lines treated with olaparib or iniparib. Data are mean±SD for uptake after 30 or 60 min of incubation with tracer (*p<0.05). All data are presented as mean±SD, n=3, unless otherwise noted.

Figure 5D:
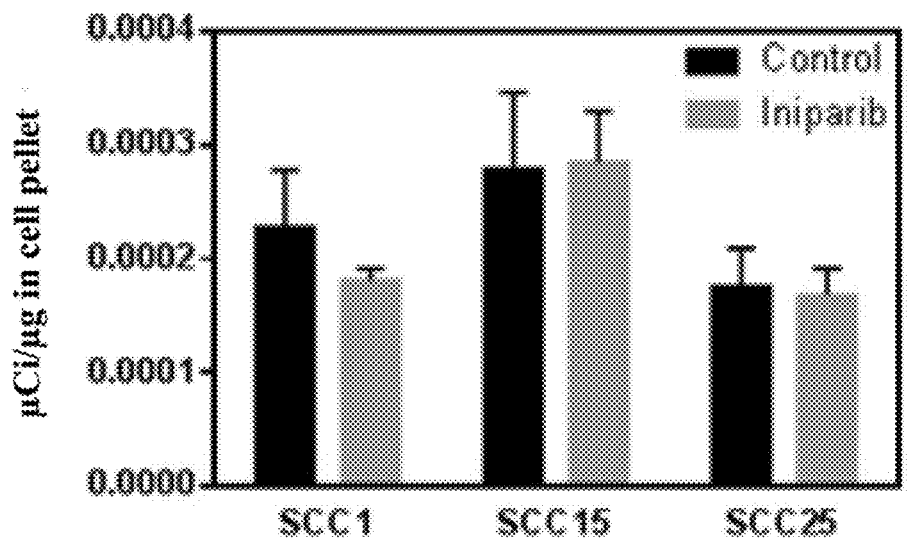

This activity is abolished by Olaparib (FIG. 5C) but not Iniparib (FIG. 5D).

Example 19

This example illustrates metabolic stability of Compound 12 ([$^{18}$F]WC-4-138).

In these experiments, the metabolic stability of [$^{18}$]-WC-4-138 was assessed after injecting 400 µCi into the tail veins of adult male C57BL/6J mice (Jackson Laboratory). Mice were sacrificed by cervical dislocation 5 or 30 minutes post-injection. The inferior vena cava was lacerated and blood was collected from the abdominal cavity. The plasma was separated from the red blood cells by centrifugation at 14000 rpm. Plasma (100 µl) was mixed with acetonitrile at a 1:1.5 ratio and centrifuged at 14000 rpm. Radioactivity associated with the red blood cell pellet, whole plasma, and acetonitrile-soluble and insoluble fractions was measured.

The liver of each animal was also collected at the indicated times and frozen on dry ice. Livers were homogenized in 2 ml acetonitrile and 1 ml of the homogenized liver was centrifuged at 14000 rpm. Radioactivity associated with the supernatant and pellet was measured.

Acetonitrile-soluble plasma or liver supernatant (100 µl) was mixed at a 1:1 ratio with water and separated by reverse phase HPLC. The parent compound was also separated by HPLC as a reference. The radioactivity associated with each HPLC fraction was measured. The percent parent compound of each sample was calculated as the portion radioactivity associated with the HPLC fractions expected to contain the parent compound.

sample was calculated as the portion of radioactivity associated with the HPLC fractions that contained the parent compound. Data are presented as mean±SD, n=3.

Four mice were sacrificed at each timepoint, with the exception of the 2 hour timepoint (n=3). Blood, heart, lung, muscle, liver, spleen, fat, adrenal glands, kidney, uterus, ovaries, bone, bone marrow, pancreas, stomach, small intestine, and large intestine were collected from each animal. All organs were blotted to remove excess blood, weighed, and counted in a Beckmann 6000 gamma counter. The percent injected dose per gram (% ID/g) of tissue was determined for each organ. Results varied from 0.5 to 1.5% infected dose per gram of tissue and are reported in Tables 1 and 2.

TABLE 1

Organ biodistribution of [$^{18}$F] WC-4-138 in athymic nude mice

| | % ID/g | | | | |
|---|---|---|---|---|---|
| | 5 min | 30 min | 60 min | 120 min | 240 min |
| Blood | 1.60 +/− 0.21 | 2.07 +/− 0.16 | 2.30 +/− 0.28 | 2.54 +/− 0.13 | 1.61 +/− 0.05 |
| Heart | 6.57 +/− 0.45 | 3.44 +/− 0.30 | 2.88 +/− 0.23 | 2.68 +/− 0.09 | 1.67 +/− 0.06 |
| Lung | 11.89 +/− 0.89 | 5.33 +/− 0.48 | 3.99 +/− 0.29 | 3.17 +/− 0.28 | 2.03 +/− 0.43 |
| Muscle | 2.05 +/− 0.48 | 2.39 +/− 0.15 | 2.21 +/− 0.31 | 2.07 +/− 0.11 | 1.35 +/− 0.09 |
| Liver | 12.50 +/− 1.08 | 8.24 +/− 0.62 | 6.50 +/− 0.52 | 4.58 +/− 0.29 | 2.43 +/− 0.25 |
| Spleen | 12.47 +/− 6.69 | 26.85 +/− 3.52 | 25.75 +/− 1.95 | 17.19 +/− 1.08 | 9.80 +/− 1.01 |
| Fat | 1.16 +/− 0.49 | 1.22 +/− 0.25 | 1.16 +/− 0.45 | 1.07 +/− 0.11 | 0.62 +/− 0.44 |
| Adrenals | 11.80 +/− 0.46 | 5.18 +/− 0.94 | 3.51 +/− 1.08 | 2.69 +/− 0.44 | 1.74 +/− 0.34 |
| Kidney | 35.63 +/− 3.33 | 21.14 +/− 2.21 | 14.02 +/− 1.84 | 8.77 +/− 0.72 | 3.67 +/− 0.54 |
| Uterus | 3.44 +/− 2.01 | 4.53 +/− 1.45 | 5.51 +/− 0.79 | 4.13 +/− 0.20 | 2.05 +/− 0.31 |
| Ovaries | 4.71 +/− 1.21 | 5.31 +/− 0.82 | 4.75 +/− 0.36 | 4.25 +/− 0.52 | 2.00 +/− 0.41 |
| Bone | 3.40 +/− 0.74 | 4.49 +/− 0.34 | 5.21 +/− 0.40 | 6.56 +/− 0.80 | 9.29 +/− 1.17 |
| Marrow | 0.06 +/− 0.02 | 0.11 +/− 0.02 | 0.13 +/− 0.04 | 0.07 +/− 0.01 | 0.04 +/− 0.01 |
| Pancress | 9.67 +/− 1.98 | 10.27 +/− 1.28 | 9.18 +/− 1.37 | 5.37 +/− 0.64 | 2.75 +/− 0.44 |
| Stomach | 3.17 +/− 0.66 | 3.77 +/− 0.73 | 3.62 +/− 0.37 | 2.56 +/− 0.27 | 1.20 +/− 0.08 |
| Small Intestine | 12.64 +/− 1.45 | 13.00 +/− 0.75 | 8.85 +/− 1.49 | 6.62 +/− 0.75 | 3.04 +/− 0.25 |
| Upper Large Intestine | 7.84 +/− 1.02 | 14.07 +/− 1.72 | 15.62 +/− 2.31 | 10.28 +/− 0.65 | 4.33 +/− 0.57 |
| Lower Large Intestine | 4.17 +/− 0.42 | 7.43 +/− 0.59 | 10.53 +/− 1.45 | 13.35 +/− 0.87 | 7.17 +/− 0.50 |
| Thyroid | 4.18 +/− 1.18 | 4.03 +/− 0.28 | 3.32 +/− 0.19 | 3.46 +/− 0.10 | 3.23 +/− 0.49 |
| Brain | 0.55 +/− 0.16 | 1.03 +/− 0.11 | 1.24 +/− 0.13 | 1.58 +/− 0.19 | 1.17 +/− 0.05 |

% ID/g = Percent injected dose per gram of tissue.
All data are mean ± SD.
n = 4 for all groups, with the exception of n = 3 at 120 min.

Figure 6:
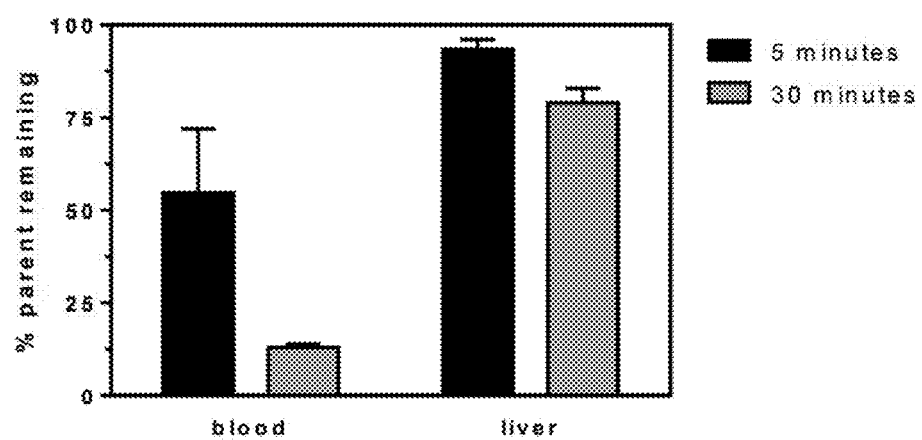
FIG. 6 illustrates metabolic stability of the [$^{18}$F]WC-4-138 tracer as evaluated in adult mice.

Compound 12 ([$^{18}$F]WC-4-138) was rapidly metabolized in the blood, with 50% relative to the reference compound present 5 minutes post-injection and only about 10% of the compound relative to the reference compound was observed 30 minutes post-injection (FIG. 6). In contrast, the compound had a much longer half-life in the liver showing about 80% relative to the reference compound 5 inmates post injection and about 70% relative to the reference compound 30 minutes post-injection (FIG. 6).

Example 20

This example illustrates biodistribution of Compound 12 ([$^{18}$F]WC-4-138) in mice. Eight week old, female, athymic nude mice (Harlan) were injected via tail vein with [$^{18}$F]WC4-138. Mice were sacrificed by cervical dislocation 5 or 30 minutes after IV tracer injection of 30 µCi, 1 or 2 hours after injection of 45 µCi, or 4 hours after injection of 60 µCi of [$^{18}$F]WC-4-138. The acetonitrile-soluble fractions of plasma or liver and the control parent compound were separated via reverse-phase high performance liquid chromatography (HPLC) and the radioactivity of each fraction was quantified. The percent parent compound of each

TABLE 2

Estimated human dosimetry from mouse biodistribution study

| Organ | Male (rad/mCi) | Female (rad/mCi) |
|---|---|---|
| Adrenals | 0.043 | 0.052 |
| Brain | 0.019 | 0.022 |
| Breasts | | 0.019 |
| Gallbladder Wall | 0.028 | 0.033 |
| LLI Wall | 0.029 | 0.036 |
| Small Intestine | 0.026 | 0.030 |
| Stomach Wall | 0.024 | 0.030 |
| ULI Wall | 0.025 | 0.031 |
| Heart Wall | 0.038 | 0.047 |
| Kidneys | 0.083 | 0.093 |
| Liver | 0.050 | 0.065 |
| Lungs | 0.035 | 0.045 |
| Muscle | 0.026 | 0.035 |
| Ovaries | | 0.045 |
| Pancreas | 0.055 | 0.064 |
| Red Marrow | 0.061 | 0.069 |
| Osteogenic Cells | 0.155 | 0.203 |
| Skin | 0.016 | 0.019 |
| Spleen | 0.110 | 0.133 |
| Testes | 0.022 | |

TABLE 2-continued

Estimated human dosimetry from mouse biodistribution study

| Organ | Male (rad/mCi) | Female (rad/mCi) |
|---|---|---|
| Thymus | 0.020 | 0.026 |
| Thyroid | 0.033 | 0.038 |
| Urinary Bladder Wall | 0.220 | 0.301 |
| Uterus |  | 0.053 |
| Total Body | 0.031 | 0.039 |
| Effective Dose Equivalent | 0.062 | 0.075 |
| Effective Dose (rem/mCi) | 0.047 | 0.057 |

Estimates were obtained from the organ residence times calculated from the mouse biodistribution data, shown in Table 1, using standard MIRD methodology.

Example 21

Figure 7:
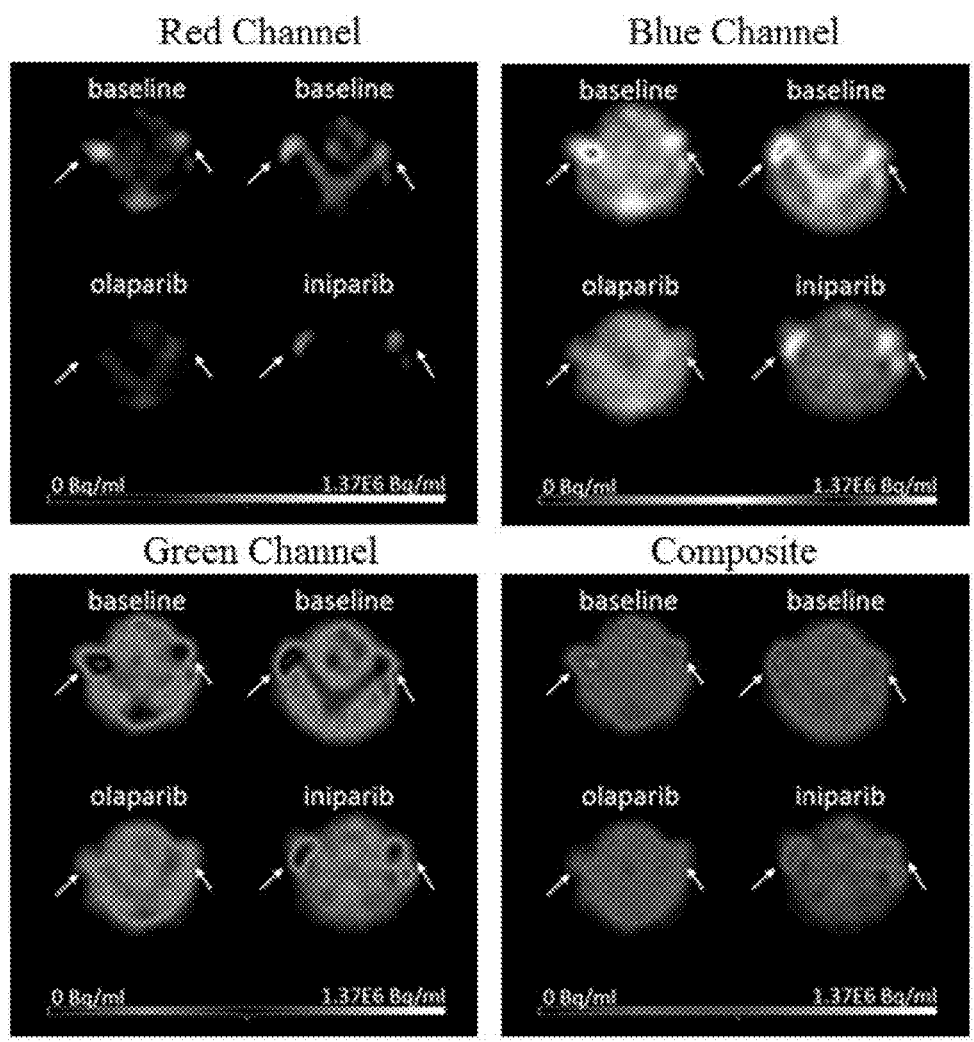
FIG. 7 illustrates MDA-MB-231 (breast cancer) tumor-bearing mice underwent dynamic imaging for 60 minutes after [$^{18}$F]WC-4-138 tracer injection.

This example illustrates uptake of Compound 12 ([$^{18}$F]WC-4-138) in mice. Mature female athymic nude mice (Charles River Laboratories) were implanted with 10$^6$ SCC1 cells or 10$^7$ MDA-MB-231 cells into the mammary fat pads. Mice bearing SCC1 tumors were imaged at 5 weeks and mice bearing MDA-MB-231 cells were imaged at 2.5 weeks after implant. Mice were anesthetized with 2% isoflurane/oxygen and maintained at 1% isoflurane/oxygen via nose cone throughout the imaging procedure. Whole animal microCT images were acquired on an Inveon PET/CT scanner. The mice were injected via tail vein with 11.36±0.5 MBq (307±13 μCi) of [$^{18}$F]WC(4)-138 and underwent a 60 minute dynamic scan using Focus 220 or Inveon PET/CT scanners. The microPET and microCT images were coregistered using Integrated Research Workflow software (Siemens). Regions of interest were drawn over tumors to determine time activity curves. For drug treatment studies, animals reached intraperitoneal injections of 50 mg/kg olaparib or iniparib 30 minutes before imaging. Mice were imaged at baseline, or 30 minutes after IP injection of olaparib or iniparib. Transverse views of MDA-MB-231 tumor-bearing mice are shown in FIG. 7. Arrows indicate location of tumors as identified on CT. Tracer is abundantly taken up in tumors and other sections of the mouse in baseline (FIG. 7, top of each channel view, arrows), but tumor uptake of [$^{18}$F]12 is abolished by treatment with olaparib (FIG. 7, bottom left of each channel panel, arrows), but tracer is still present in other areas of the section. In contrast, iniparb treatment does not effect the uptake of [$^{18}$F]WC(4)-138 in tumor cells, but abolishes said uptake in other types of cells (FIG. 7, bottom right of each channel view, arrows).

Example 22

Figures 8A, 8B:
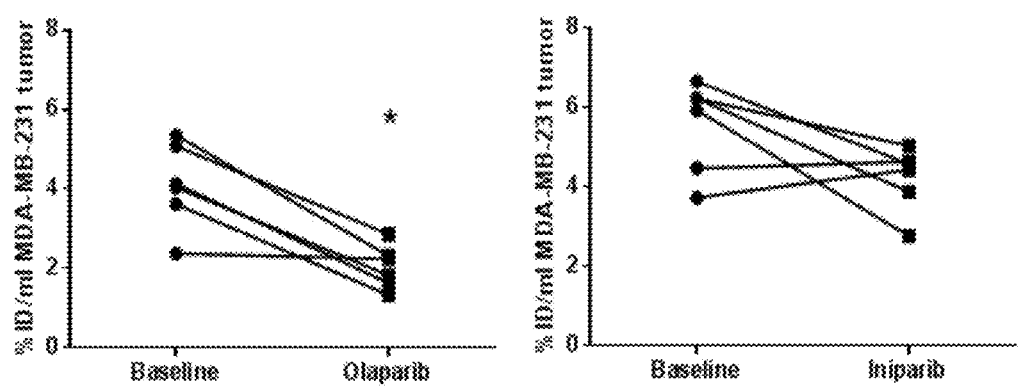
FIG. 8A-B illustrates MDA/MB-231 (breast cancer) or SCC1 (HNSCC) tumor-bearing mice that underwent dynamic imaging for 60 minutes after [$^{18}$F]WC-4-138 tracer injection.

This example illustrates a quantitative analysis that shows significant decreases in injected dose per ml between baseline and drug treatment for both MDA-MB-231 tumors (FIG. 8A) and SCC tumors (FIG. 8B). In FIG. 8, mice were imaged at baseline, or 30 minutes after IP injection of olaparib or iniparib. (A) The percent of injected dose per ml was calculated for each MDA/MB-231 tumor at baseline or after drug treatment. Tracer uptake was significantly reduced in olaparib-treated mice (*p=0.0038 as determined by a paired t test, n=6 tumors). Tracer uptake was unchanged in iniparib-treated mice (p=0.1098 as determined by a paired t test, n=6 tumors). (B) The percent of injected dose per ml was calculated (or each SCC1 tumor at baseline or after drug treatment. Tracer uptake was significantly reduced in olaparib-treated mice (*p=0.001 as determined by a paired t test, n=8 tumors). Tracer uptake was unchanged in iniparib-treated mice (p=0.7216 as determined by a paired t test, n=5 tumors).

Example 23

A subject presents with symptoms of potential PARP-1 associated breast cancer. A physician orders PET scanning, and a technician administers an effective amount of [$^{18}$F]WC(4)-138 and performs the PET scan. The tumor exhibits a large amount of tracer uptake compared to the surrounding tissues of the subject. The physician diagnoses PARP-1 associated cancer and prescribes PARP-1 inhibitors as part of a treatment regime.

Example 24

A subject presents with abnormal inflammation of the lungs. A physician orders PET scanning, and a technician administers an effective amount of [$^{18}$F]WC(4)-138 and performs the PET scan. The lung tissue exhibits large amounts of tracer uptake relative to control lung tissue, and the physician diagnoses PARP-1 related inflammation and prescribes PARP-1 inhibitors as part of a treatment regime.

REFERENCES

1. Hassa, P. O.; Hottiger, M. O. Frontiers in Bioscience: a Journal and Virtual Library 2008, 13, 3046.
2. d'Adda di Fagagna, F.; Hande, M. P.; Tong, W. M.; Lansdorp, P. M; Wang, Z. Q.; Jackson, S. P. Nature Genetics 1999, 23, 76.
3. Jagtap, P.; Szabo, C. Nature Reviews, Drug Discovery 2005, 4, 421.
4. Schreiber, V.; Dantzer, F.; Ame, J. C.; de Murcia, G. Nature Reviews. Molecular Cell Biology 2006, 7, 517.
5. Virag, L.; Szabo, C. Pharmacological Reviews 2002, 54, 375.
6. Gradwohl, G.; Menissier de Murcia, J. M.; Molinete, M.; Simonin, F.; Koken, M.; Hoeijmakers, J. H.; de Murcia, G. Proceedings of the National Academy of Sciences of the United States of America 1990, 87, 2990.
7. Kameshita, L.; Matsuda, Z.; Taniguchi, T.; Shizuta, Y. The Journal of Biological Chemistry 1984, 259, 4770.
8. Ferraris, D. V. Journal of Medicinal Chemistry 2010, 53, 4561.
9. Basu, B.; Sandhu, S. K.; de Bono, J. S. Drugs 2012, 72, 1579.
10. Sandhu. S. K.; Schelman, W. R.; Wilding, G.; Moreno, V.; Baird, R. D.; Miranda, S.; Hylands, L.; Riisnaes, R.; Forster, M.; Omlin, A.; Kreischer, N.; Thway, K.; Gevenslehen, H.; Sun, L.; Loughney, J.; Chatterjee, M.; Toniatti, C.; Carpenter, C. L.; Iannoue, R.; Kaye, S. B.; de Bono, J. S.; Wenham, R. M. The Lacet Oncology 2013, 14, 882.
11. Plummer, R.; Lorigan, P.; Steven, N.; Scott, L.; Middleton, M. R.; Wilson, R. H.; Mulligan, E.; Curtin, N.; Wang, D.; Deji, R.; Abbattisia, A.; Gallo, J.; Calvert. H. Cancer Chemotherapy and Pharmacology 2013, 71, 1191.
12. Gelmon, K. A.; Tischkowitz, M.; Mackay, H.; Swenerton, K.; Robidoux, A.; Tonkin K.; Hirte, H.; Huntsman, D.; Clemons, M.; Gilks, B.; Yerushalmi, R.; Macpherson, E.; Carmichael J.; Oza, A. The Lancet Oncology 2011, 12, 852.

13. Kummar, S.; Chen, A.; Ji, J.; Zhang, Y.; Reid, J. M.; Ames, M.; Jia, L.; Weil M.; Speranza, G.; Murgo, A. J.; Kinders, R.; Wang, L.; Parchment, R. E.; Carter, J.; Stotler, H.; Rubinstein, L.; Hollingshead, M.; Melillo, G.; Pommier, Y.; Bonner, W.; Tomaszewski, J. E.; Doroshow, J. H. Cancer Research 2011, 71, 5626.
14. Javle, M.; Curtin, N, J. Therapeutic Advances in Medical Oncology 2011, 3, 257.
15. Wahlberg, E.; Karlberg, T.; Kouznetsova, E.; Markova, N.; Macchiarulo, A.; Thorsell, A. G.; Pol, E.; Frostell, A.; Ekblad, T.; Oncn, D.; Kull, B.; Robertson, G. M.; Pellicciari, R.; Schuler, H.; Weigelt J. Nature Biotechnology 2012,30, 283.
16. Liu, X.; Shi, Y.; Maag, D. X.; Palma, J. P.; Patterson, M. J.; Ellis, P. A.; Surber, B. W.; Ready, D. B.; Soni, N. B.; Ladror, U. S.: Xu, A. J.; Iyer, R.; Harlan, J. E.; Solomon, L. R.; Donawho, C, K.; Penning, T. D.; Johnson, E. F.; Shoemaker, A. R. Clinical Cancer Research: an Official Journal of the American Association for Cancer Research 2012, 18, 510.
17. Tu, Z.; Chu, W.; Zhang, J.; Dence, C. S.; Welch, M. J.; Mach, R. H. Nuclear Medicine and Biology 2005, 32,437.
18. Keliher, E. J.; Reiner, T.; Turetsky, A.; Hilderbrand, S. A.; Weisslecler, R. ChemMedChem 2011, 6, 424.
19. Reiner, T.; Keliher, E. J.; Earley, S.; Marinelli, B.; Weissleder, R. Angew Chem Int Ed Engl 2011, 50, 1922.
20. Reiner, T.; Lacy. J.; Keliher, E. J.; Yang, K. S.: Ullal, A.; Kohler, R. H.; Vinegoni, C.; Weissleder. R. Neoplasia 2012, 14, 169.
21. Delaney. C. A.; Wang, L. Z.; Kyle, S.; White, A. W.; Calvert, A, H.; Curtin, N. J.; Durkacz, B. W.; Hostomsky, Z.; Newell, D. R. Clinical cancer research; an official journal of the American Association for Cancer Research 2000, 6, 2860.
22. Skalitzky, D. J.; Marakovits, J. T.; Maegley. K. A.; Ekker, A.; Yu, X. H.; Hostomsky, Z.; Webber. S. E.; Eastman, B. W.; Almassy, R.; Li. J.; Curtin, N. J.; Newell. D, R.; Calvert, A. H.; Griffin, R. J.; Golding. B. T. Journal of Medicinal Chemistry 2003, 46, 210.
23. Putt, K. S.; Hergenrother, P. J. Analytical Biochemistry 2004, 326, 78.
24. Jagtap, P.; Soriano, F. G.; Virag, L.; Liaudet. L.; Mabley, J.; Szabo, E.; Hasko, G.; Marton, A.; Lorigados, C. B.; Gallyas, F., Jr.; Sumegi, B.; Hoyt, D. G.; Baloglu, E.; VanDuzer, J.; Salzman, A. L.; Southan, G. J.; Szabo, C. Critical Care Medicine 2002, 30, 1071.
25. Ruf, A.; de Murcia, G.; Schulz, G. E. Biochemistry 1998, 37, 3893.
26. Kinoshna, T.; Nakanishi, I.; Warizaya, M.; Iwashita, A.; Kido, Y.; Hattori, K.; Fujii, T. FEBS letters 2004, 556, 43.
27. White, A. W.; Almassy, R.; Calvert, A. H.; Curtin, N. J.; Griffin, R. J.; Hostomsky, Z.; Maegley, K.; Newell, O. R.; Srinivasan, S.; Golding, B. T. Journal of Medicinal Chemistry 2000, 43, 4084.
28. Lasne, M. C.; Perrio, C.; Rouden, J.; Barre, L.; Roeda, D.; Dolle, F.; Crouzel, C. Top Curr Chem 2002, 222, 201.
29. Glaser, M.;. Arstad, E. Bioconjugate chemistry 2007, 18, 989.
30. Zhou, D.; Chu, W.; Dence, C. S.; Mach, R. H.; Welch, M. J. Nuclear Medicine and Biology 2012.
31. Menear, K. A.; Adcock, C.; Boulter, R.; Cockcroft, X. L.; Copsey, L.; Cranston, A.; Dillon, K. J.; Drzewiecki, J.; Garman, S.; Gomez, S.; Javaid, H.; Kerrigan, F.; Knights, C.; Lau, A.; Loh, V. M. Jr.; Matthews, I. T.; Moore, S.; O'Connor, M. J.; Smith, G. C.; Martin, N. M. journal of Medicinal Chemistry 2008, 51, 6581.

All publications cited herein are incorporated by reference, each in its entirety. As used herein, the singular forms "a", "an" and "the" are intended to include the plural forms as well, unless the context indicates otherwise.

What is claimed is:

1. A compound or pharmaceutically acceptable salt thereof of structure

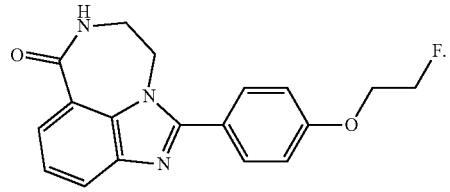 [SMILES: O=C1NCCn2c(-c3ccc(OCCF)cc3)nc3cccc1c32]

2. The compound or pharmaceutically acceptable salt thereof according to claim 1, wherein the fluorine designated F is an $^{18}$F fluorine.

3. A method of imaging a tissue in a subject, comprising: administering to a subject a compound or pharmaceutically acceptable salt thereof of structure

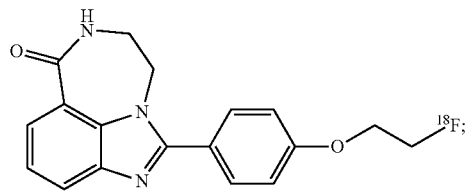

and
  subjecting the subject to positron emission tomography (PET) scanning.

4. The method of imaging a tissue in a subject according to claim 3, wherein the tissue is a tumor tissue.

5. The method of imaging a tissue in a subject according to claim 3, wherein the tissue is an inflamed tissue.

* * * * *